(12) United States Patent
Slager

(10) Patent No.: US 8,697,105 B2
(45) Date of Patent: Apr. 15, 2014

(54) INJECTABLE DRUG DELIVERY FORMULATION

(75) Inventor: Joram Slager, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 331 days.

(21) Appl. No.: 13/074,212

(22) Filed: Mar. 29, 2011

(65) Prior Publication Data

US 2011/0236454 A1    Sep. 29, 2011

Related U.S. Application Data

(60) Provisional application No. 61/318,717, filed on Mar. 29, 2010.

(51) Int. Cl.
| | | |
|---|---|---|
| *A61F 13/00* | (2006.01) | |
| *A61K 9/00* | (2006.01) | |
| *A61K 38/00* | (2006.01) | |
| *A61K 31/7088* | (2006.01) | |
| *A61K 47/30* | (2006.01) | |
| *A61K 47/36* | (2006.01) | |
| *A61P 27/06* | (2006.01) | |
| *A61P 27/12* | (2006.01) | |

(52) U.S. Cl.
USPC ............ 424/422; 424/486; 424/488; 514/1.1; 514/44; 514/772.3; 514/777

(58) Field of Classification Search
USPC ...................... 424/422, 426, 78.27; 525/54.1; 536/123.1
See application file for complete search history.

(56) References Cited

U.S. PATENT DOCUMENTS

| 4,938,949 A | 7/1990 | Borch et al. |
| 7,638,344 B2 | 12/2009 | Slager et al. |
| 2003/0153001 A1* | 8/2003 | Soane et al. ................. 435/7.1 |
| 2007/0218102 A1 | 9/2007 | Chudzik et al. |
| 2007/0224247 A1 | 9/2007 | Chudzik et al. |
| 2007/0260054 A1 | 11/2007 | Chudzik |

FOREIGN PATENT DOCUMENTS

| WO | WO-2007/035886 A1 | 3/2007 |
| WO | WO-2008/060359 A2 | 5/2008 |
| WO | WO-2009/005718 A1 | 1/2009 |
| WO | WO-2009/038783 A1 | 3/2009 |
| WO | WO-2009/134344 A1 | 11/2009 |
| WO | WO-2010/047799 A1 | 4/2010 |
| WO | WO-2010/141553 A1 | 12/2010 |
| WO | WO-2011/123416 A1 | 10/2011 |

OTHER PUBLICATIONS

Rosenfeld et al., "Ranibizumab for Neovacular Age-Related Macular Degeneration." The New England Journal of Medicine 2006:255(14);1419-1431.*
"International Application Serial No. PCT/US2011/030271, International Search Report mailed Jul. 26, 2011", 5 pp.
"International Application Serial No. PCT/US2011/030271, Written Opinion mailed Jul. 26, 2011", 9 pp.

* cited by examiner

*Primary Examiner* — Walter Webb
(74) *Attorney, Agent, or Firm* — Pauly, Devries Smith & Deffner LLC.

(57) ABSTRACT

The invention provides an injectable formulation that includes an active agent; a biocompatible solvent system, crosslinkable polymers such as polysaccharides; and crosslinking agents; wherein the formulation is substantially free of water. The invention also provides a drug delivery depot formed from the injectable formulation wherein the polymers crosslink in the presence of water in the body of a patient, or in the air, prior to implantation in the patient. Also provided are methods of treatment using such formulations and drug delivery systems.

19 Claims, 2 Drawing Sheets

Figure 1

INJECTABLE DRUG DELIVERY FORMULATION

RELATED APPLICATIONS

This application claims priority to U.S. Ser. No. 61/318,717 filed on Mar. 29, 2010, which is incorporated by reference herein in its entirety.

BACKGROUND

Several challenges face patients and physicians in the area of drug delivery. Examples of challenging areas of drug delivery include ocular drug delivery, subcutaneous drug delivery, and sustained release of the drug to be delivered. Many current therapies require repetitive treatments, such as multiple injections, multiple topical applications, or multiple series of eye drops per day. Other drug delivery systems, such as topically applied medications, can have a peak effect within a few hours. Repeated treatments are then also required for these delivery systems. The repetitive nature of these treatments often results in reduced efficacy because of poor patient compliance. The lack of patient compliance and the associated economic costs of repeated treatments can thus lead to ineffective treatments, further medical complications, and deterioration of the patient's health. Premature depletion and/or release of a drug from an implant or depot can result in undesired initial burst and thereafter insufficient drug being delivered for a portion of the treatment period. Accordingly, there is a need for improved drug delivery systems, such as improved drug depots or implants, that overcome one or more of the shortcomings of current commercial drug delivery systems discussed above.

SUMMARY

The invention provides an injectable formulation that includes an active agent; a biocompatible solvent system; polymers that can be crosslinked, such as those having two or more hydroxyl groups; and crosslinking agents; wherein the formulation is substantially free of water. The invention also provides a drug delivery depot formed from the injectable formulation wherein the polymers crosslink in the presence of water in the body of a patient. Also provided are methods of treatment using such formulations and drug delivery systems.

Accordingly, in one embodiment, the invention provides an injectable formulation comprising: an active agent;

a non-aqueous, aprotic, biocompatible solvent system, wherein the solvent system comprises one or more solvents and at least one of the solvents is non-miscible with water;

a plurality of polymers that include a plurality of hydroxyl groups; and a plurality of crosslinking agents, wherein the crosslinking agent comprises X—$(C_1$-$C_{16})$alkyl-X or X—$(CH_2CH_2$—O$)_n$—$CH_2CH_2$—X where "n" is 0 to about 20, and each X is independently a chlorosilane group, a trialkoxysilane group, or —NCO.

The solvent system can be chemically inert with respect to the crosslinking agents and the formulation can be substantially free of water.

The invention also provides an in vivo or ex vivo biodegradable crosslinked matrix comprising: a non-aqueous aprotic biocompatible solvent system wherein the solvent system comprises one or more solvents and at least one of the solvents is non-miscible with water;

a plurality of polymers that include a plurality of hydroxyl groups, where a plurality of the polymers are crosslinked by:
—$(Y)_2Si$—$(C_1$-$C_{16})$alkyl-$Si(Y)_2$— groups;
—$(Y)_2Si$—$(CH_2CH_2$—O$)_n$—$CH_2CH_2$—$Si(Y)_2$— groups where n is 0 to about 20;
—C(=O)NH—$(C_1$-$C_{16})$alkyl-$Si(Y)_2$— groups;
—C(=O)NH—$(CH_2CH_2$—O$)_n$—$CH_2CH_2$—$Si(Y)_2$— groups where n is 0 to about 20;
—C(=O)NH—$(C_1$-$C_{16})$alkyl-NH—C(=O)— groups;
—C(=O)NH—$(CH_2CH_2$—O$)_n$—$CH_2CH_2$—NH—C(=O)— groups where n is 0 to about 20; or a combination thereof; where each Y is independently —OH, —O-alkyl, or alkyl; and an active agent that is dissolved or dispersed throughout the crosslinked matrix.

The plurality of polymers that include a plurality of hydroxyl groups can be optionally substituted polysaccharides. The polysaccharides can have a base molecular weight of about 10 kDa to about 500 kDa, and the polysaccharides can have a degree of substitution of about 0.25 to about 2. The substituents of the polysaccharides can include optionally substituted $(C_2$-$C_{12})$alkanoate groups, and the polysaccharides can be crosslinked at the location of free hydroxyl groups of the polysaccharides, and/or at hydroxyl groups that are substituents on the alkanoate groups, when present.

The invention further provides a method of delivering an active agent to a subject comprising injecting a formulation into the tissue of a patient, or injecting the formulation ex vivo, allowing the resulting matrix to crosslink by contact with ambient humidity to form an implant, followed by inserting the resulting implant into the patient. The formulation can include: an active agent;

a non-aqueous, aprotic, biocompatible solvent system, wherein the solvent system comprises one or more solvents and at least one of the solvents is non-miscible with water;

a plurality of polymers that each include a plurality of hydroxyl groups; and a plurality of crosslinking agents, wherein the crosslinking agent comprises X—$(C_1$-$C_{16})$alkyl-X or X—$(CH_2CH_2$—O$)_n$—$CH_2CH_2$—X where "n" is 0 to about 20, and each X is independently a chlorosilane group, a tri$(C_1$-$C_3)$alkoxysilane group, or —NCO;

wherein the solvent system is chemically inert with respect to the crosslinking agents and the formulation is substantially free of water; and the formulation forms a gel matrix within the subject and the gel matrix becomes crosslinked when the hydroxyl-substituted polymers and crosslinking agents are contacted by fluids in the body of the subject or by ambient humidity; and the matrix releases the active agent, over a period of weeks, to the body of the subject; thereby delivering the active agent to the subject.

The invention therefore provides novel polymers and compositions thereof, and intermediates for the synthesis of such polymers and compositions, as well as methods of preparing the polymers and compositions. The invention also provides polymers and compositions that are useful as intermediates for the synthesis of other useful polymers and compositions. The invention additionally provides for the use of the polymers and compositions for the treatment of various conditions or diseases in a mammal. The diseases or conditions can include diseases or conditions that affect the eye, cardiovascular diseases, tumors such as cancer tumors, and/or the formulation can be used for pain management, and the formulation can include corresponding active agents that treat such diseases.

The present invention also provides for the formulations and/or compositions described herein, for the treatment of a disease. More specifically, the present invention also provides for the formulations and/or compositions described herein, for the treatment of at least one of the following diseases or disorders: keratoconjunctivitis sicca (KCS) or dry eye syndrome; aphakia; pseudophakia; blepharospasm; cataract; conjunctival diseases; conjunctivitis; corneal diseases; corneal ulcer; eyelid diseases; lacrimal apparatus diseases; lacrimal duct obstruction; myopia; presbyopia; pupil disorders; refractive disorders and strabismus, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema (DME); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 1 illustrates controlled release experiments where the release of 20 wt. % Fab from various crosslinked organogels formed from chlorosilane derived crosslinking moieties was monitored for more than 70 days.

DETAILED DESCRIPTION

Figure 2:
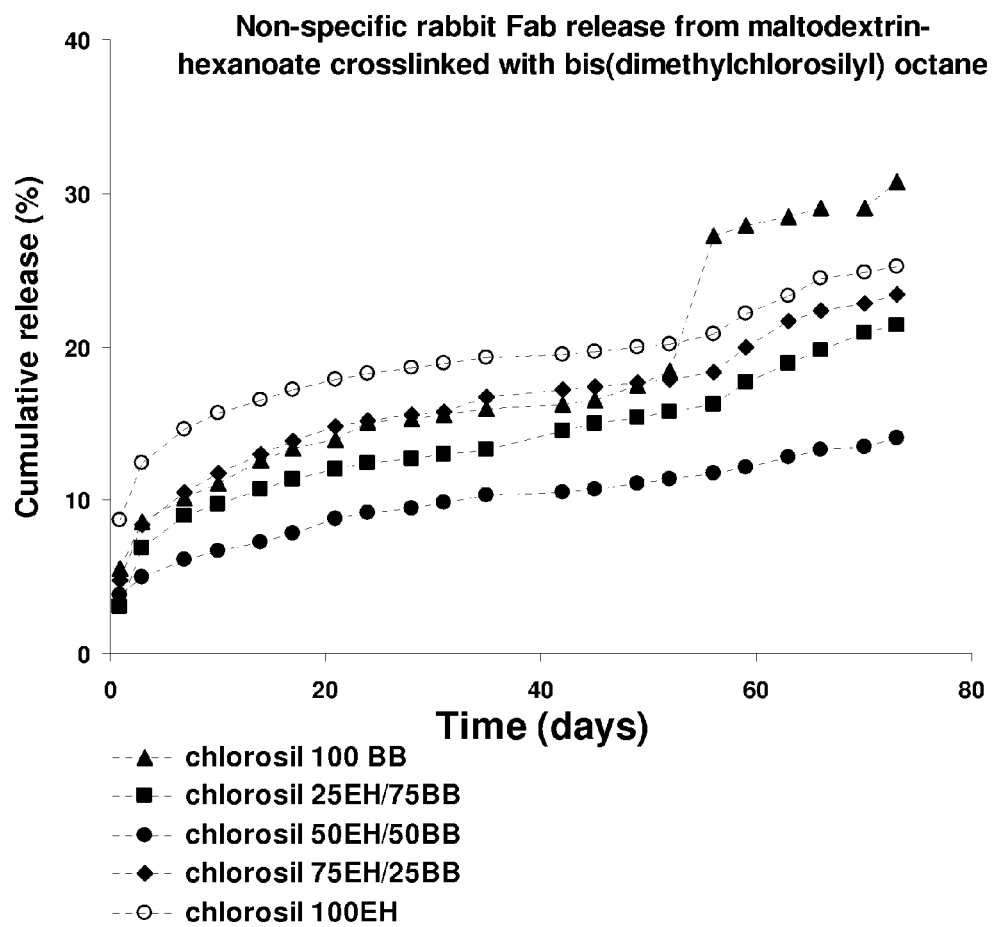
FIG. 2 illustrates controlled release experiments where the release of 20 wt. % Fab from various organogels formed from trimethoxysilane derived crosslinking moieties was monitored for more than 70 days.

The invention provides polymers, compositions, and methods that help overcome many of the challenges faced by drug delivery, particularly drug delivery by injection. One method includes administering to a subject by injection a composition described herein, where after injection, the composition forms an organogel implant (or "drug depot") that provides an active agent to the subject over a prolonged period of time. The injection can be, for example, ocular, subcutaneous, or intramuscular. The organogel implant crosslinks in vivo over a period of time, which increases the viscosity, rigidity, and/or stability of the implant, thereby improving the implant drug release profile. The active agent can be locally or systemically delivered to the subject, and the subject can be a mammal, for example, a human.

The formulation can be administered to the subject about once a week to about once per 6 months, to effectively treat a diseases or disorders, such as condition or disease described herein. The diseases or conditions can include diseases or conditions that affect the eye, cardiovascular diseases, tumors such as cancer tumors, and/or the formulation can be used in pain management. The formulation can include a corresponding active agent that treats such conditions. A biodegradable organogel implant formed in vivo can biodegrade within a few months to about a year. Eventually, the implant can substantially or completely biodegrade and a final amount of active agent is thereby delivered to the patient from the implant.

Accordingly, in one embodiment, the invention provides an injectable formulation comprising an active agent; a non-aqueous aprotic biocompatible solvent system, a plurality of polymers that each include a plurality of hydroxyl groups; and crosslinking agents. The solvent system can be chemically inert with respect to the crosslinking agents and the formulation can be free of, or substantially free of, water, acid, base, or a protic solvent. In some embodiments, water, acid, base, and/or a protic solvent can be added to the formulation to facilitate crosslinking. In another embodiment, the hydroxyl-substituted polymers can be exchanged in the formulation for another suitable polymer that is crosslinkable, for example, a polymer that has one or more hydroxyl groups on each monomer or on pendant groups of the monomers, or that has one or more blocks that have hydroxyl groups that can be used for crosslinking. In one embodiment, the polymer can be an optionally substituted polysaccharide. In some embodiments, the polymer is a polymer that has two or more hydroxyl groups that can be used to crosslink the polymers to form a drug delivery matrix.

Accordingly, in one embodiment, the invention provides an injectable formulation comprising: an active agent; a non-aqueous, aprotic, biocompatible solvent system, wherein the solvent system comprises one or more solvents and at least one of the solvents is non-miscible with water; a plurality of optionally substituted polysaccharides; and a plurality of crosslinking agents, where the crosslinking agent comprises X—($C_1$-$C_{16}$)alkyl-X or X—($CH_2CH_2$—O)$_n$—$CH_2CH_2$—X where "n" is 0 to about 20, and each X is independently a chlorosilane group, a trialkoxysilane group, or —NCO. The solvent system can be chemically inert with respect to the crosslinking agents and the formulation can be substantially free of water. In some embodiments, the polysaccharides can have a base molecular weight of about 10 kDa to about 500 kDa. In some embodiments, the polysaccharides can also have a degree of substitution by optionally substituted ($C_2$-$C_{12}$)alkanoate groups of about 0.25 to about 2.

The active agent can be present in about 0.1 wt. % to about 30 wt. % of the formulation, the solvent system can be present in about 10 wt. % to about 90 wt. % of the formulation, the polymer can be present in about 5 wt. % to about 50 wt. % of the formulation, and the crosslinking agents can be present in about 0.5 wt. % to about 50 wt. % of the formulation. As would be readily recognized by one skilled in the art, the weight percentages of each component can be adjusted within the above ranges at increments of 0.5 wt. %, 1 wt. %, or 5 wt. %, throughout the recited ranges.

The crosslinking agents provide significant additional viscosity, stability, elasticity, and/or drug release control in the resulting crosslinked organogel. The crosslinking agent can be present in about 0.5 wt. % to about 50 wt. % of the formulation. In other embodiments, the crosslinking agent can be present in about 0.5 wt. % to about 50 wt. %, about 1 wt. % to about 40 wt. %, about 2 wt. % to about 30 wt. %, about 5 wt. % to about 25 wt. %, about 7.5 wt. % to about 20 wt. %, or about 10 wt. % to about 20 wt. %, of the formulation. In some embodiments, the crosslinking agent is present in about 0.5 wt. %, about 1 wt. %, about 2 wt. %, about 5 wt. %, about 7.5 wt. %, about 10 wt. %, about 12.5 wt. %, about 15 wt. %, about 20 wt. %, or about 30 wt. %, of the formulation.

In one embodiment, the amount of the solvent system is selected to provide a formulation that has a concentration of the hydroxyl-substituted polymer of about 50 mg/mL to about 500 mg/mL, or about 100 mg/mL, about 200 mg/mL, about 250 mg/mL, about 300 mg/mL, about 350 mg/mL, about 400 mg/mL, or about 500 mg/mL.

In one embodiment, the polymer can be soluble in the biocompatible solvent system and the active agent can be substantially insoluble in the non-aqueous biocompatible solvent system. The composition can be a homogenous suspension such that the active agent is homogeneously dispersed (e.g., undissolved, unsolubilized and/or suspended) throughout the composition. When the formulation is in the presence of moisture, such as in vivo, the formulation can form an implant and the active agent can be homogeneously suspended throughout the implant. In some embodiments, the resulting solid biodegradable implant is monolithic.

The molar ratio of reactive groups on the crosslinking agents to free hydroxyl groups of the polymer can be about 0.1 (reactive groups on the crosslinking agents per to free hydroxyl group on average) to about 5. Other molar ratios can also be used, such as about 0.5, about 0.75, about 1, about 1.3, about 1.5, about 1.75, about 2, about 2.5, about 3, about 4, or about 4.5.

The active agent can be any suitable agent that can be delivered to a patient using the crosslinkable formulation. Examples of active agents include peptides such as leuprolide and somatostatin; proteins such as therapeutic antibodies, fractions of antibodies (Fab), erythropoietin, and insulin; genes, polynucleotides such as miRNA, siRNA, and DNA, or analogs or complexes thereof, nucleotides, nucleosides, or small molecule drugs such as triamcinolone acetonide, temozolomide, rapamycin, dexamethasone, and paclitaxel, as well as PEGylated proteins, PEGylated aptamers, enzymes, blood clotting factors, growth factors, cytokines, hormones, or vaccines.

Administration of the formulations described herein is not limited to injection. In some embodiments, the formulation is injected into a subject or patient to form an implant. In other embodiments, the implant is formed ex vivo and then placed within the patient, such as during the course of surgery. Thus, the implant can be administered as a leave-behind product and inserted into a body cavity existing after completion of surgery. Alternatively, it can be applied as a flowable gel by brushing the gel onto residual tissue or bone. Use of the formulations described herein can permit loading of active agents in the gel above concentrations typically present with currently known injectable compositions that are limited by solubility parameters.

The active agent can be incorporated into the formulation in the form of particles. In some embodiments, the particles can be suspended in the formulation, thereby forming a suspension. The particles can have an average particle size of about 0.1 to about 100 microns, from about 1 to about 25 microns, from about 1 to about 20 microns, from about 0.1 to about 10 microns, or from about 2 to about 10 microns. In some embodiments, the particles can have an average particle size of at least about 0.1 or about 1 micron and less than about 25, 20, 15, or microns. For instance, particles having an average particle size of about 5 microns have been produced by spray drying or freeze drying an aqueous mixture containing 50% sucrose and 50% lysozyme (on a dry weight basis) and mixtures of hGH (e.g., 5-30% or 10-20%) and zinc acetate (e.g., 10-40 mM or 15-30 mM). Other particles can be prepared by spray drying or freeze drying an aqueous mixture containing 70% Fab protein and 30% trehalose. Such particles can be used in conjunction with the examples described below. Conventional lyophilization processes can also be used to form particles of beneficial agents of varying sizes using appropriate freezing and drying cycles. As such, the active agent can be in the form of a spray-dried protein, such as Fab or IgG.

To form a suspension of particles of the active agent in the crosslinkable composition, any conventional low shear device can be used, such as an AKI25T or Silverson™ mixer, or a Ross double planetary mixer, for example, at ambient conditions. In this manner, efficient distribution of the active agent can be achieved substantially without degrading the active agent.

The formulation in the biocompatible solvent system, before crosslinking, can have a viscosity of at least about 100 cP at 37° C., or about 100 cP to about 1000 cP, and up to about 50,000 cP at room temperature. Although viscous, the composition can be formulated as an injectable delivery system, for example, for administration through a needle. The delivery system can be an injectable ocular delivery system, an injectable subcutaneous delivery system or an injectable parenteral delivery system. As such, the composition can be flowable and can be formulated for injection through a needle. In some embodiments, the needle can be a small diameter needle such as a 25 gauge needle, or a higher gauge needle (e.g., a 30 gauge needle). In other embodiments, such as for intramuscular injection, the needle can be a larger diameter needle such as a 14 gauge needle or an 18 gauge needle. In some embodiments, the volume of the delivery system is a volume that is suitable for injection into a patient. For example, suitable injection volumes can be about 10 μL to about 100 μL, or about 0.01 mL to about 2.0 mL. The injectable delivery system is thus suitable for forming an implant (e.g., a controlled-release implant) in vivo.

The crosslinking agent can be any suitable crosslinker with two reactive groups such that the crosslinker can link two polymers together, for example, when exposed to bodily fluids, by reacting with corresponding reactive groups on the polymer, for example, hydroxyl groups on a hydroxyl-substituted polymer, such as, but not limited to, a polysaccharide. In some embodiments, the crosslinking agent can be X—($C_1$-$C_{16}$)alkyl-X or X—($CH_2CH_2$—O)$_n$—$CH_2CH_2$—X where "n" is 0 to about 20. Each X can be independently a chlorosilane group, a trialkoxysilane group, or an isocyanate group (—NCO). The chlorosilane group can be, for example, —Si(Me)$_2$Cl, —Si(Et)$_2$Cl, or —Si(Ph)$_2$Cl. The trialkoxysilane group can be, for example, a tri($C_1$-$C_3$)alkoxy-silane group, such as —Si(OMe)$_3$ or —Si(OEt)$_3$. The groups X can also be an isocyanate group, or each X can independently be any of the preceding groups.

To provide a delayed release drug delivery implant or depot, the injectable formulation can be injected into a patient, which results in the formation of an organogel implant. Upon contact with bodily fluid, the crosslinking agents begin to crosslink the organogel to form a more stable matrix that modulates the escape of the active agent to the patient, thereby providing a prolonged release period of the active agent. Accordingly, an in vivo biodegradable crosslinked matrix is formed, wherein biodegradable crosslinked matrix includes a non-aqueous aprotic biocompatible solvent system, wherein the solvent system can include one or more solvents and at least one of the solvents is non-miscible with water; a plurality of crosslinked polymers. In one embodiment, the polymers can be substituted polysaccharides that have a base molecular weight of about 10 kDa to about 500 kDa, and that have a degree of substitution of about 0.25 to about 2, wherein the substituents of the polysaccharides comprise optionally substituted ($C_2$-$C_{12}$)alkanoate groups. The polymers can be crosslinked by:

—(Y)$_2$Si—($C_1$-$C_{16}$)alkyl-Si(Y)$_2$— groups;

—(Y)$_2$Si—(CH$_2$CH$_2$—O)$_n$—CH$_2$CH$_2$—Si(Y)$_2$— groups where n is 0 to about 20;

—C(=O)NH—($C_1$-$C_{16}$)alkyl-Si(Y)$_2$— groups;

—C(=O)NH—(CH$_2$CH$_2$—O)$_n$—CH$_2$CH$_2$—Si(Y)$_2$— groups where n is 0 to about 20;

—C(=O)NH—($C_1$-$C_{16}$)alkyl-NH—C(=O)— groups;

—C(=O)NH—(CH$_2$CH$_2$—O)$_n$—CH$_2$CH$_2$—NH—C(=O)— groups where n is 0 to about 20; or a combination thereof; where each Y is independently —OH, —O-alkyl, or alkyl. The formulation can further include an active agent that is dissolved or dispersed throughout the crosslinked matrix.

The degree of crosslinking of each polymer can average about 2 per polymer chain to about 2 per monomer of each polymer. For example, when the polymer is a polysaccharide, the degree of crosslinking of each polysaccharide can average about 0.1 to about 2 per monomer of the polysaccharide. Less than 20 wt. % of the active agent is typically released from the matrix in the first 20 days of deposit within a subject. In other embodiments, less than 20 wt. % of the active agent is released from the matrix within the first 40 days, first 7 days, 5 days, or 72 hours, of deposit within a subject, depending on the active agent and the degree of crosslinking engineered into the implant.

After the formulation is injected into a patient, the non-aqueous biocompatible solvent system in the matrix maintains the active agent in the resulting implant. As the amount of the non-aqueous biocompatible solvent system in the matrix decreases over time and the matrix biodegrades over time by natural degradation processes in the body of the patient, the active agent is released into the body of the patient.

In one embodiment, hydroxyl-substituted polymer of the formulation can be a crosslinked substituted polysaccharides of Formula I:

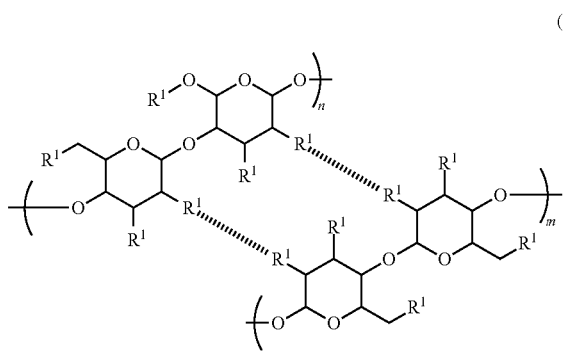

(I)

wherein each $R^1$ is independently OH, —OSi(alkyl)$_3$ or an optionally substituted ($C_2$-$C_{12}$)alkanoate, or any two $R^1$ groups together form a crosslinking moiety, wherein each crosslinking moiety is independently:

—OSi(Y)$_2$—($C_1$-$C_{16}$)alkyl-Si(Y)$_2$O—;

—OSi(Y)$_2$—(CH$_2$CH$_2$—O)$_n$—CH$_2$CH$_2$—Si(Y)$_2$O— where n is 0 to about 20;

—O—C(=O)NH—($C_1$-$C_{16}$)alkyl-Si(Y)$_2$O—;

—O—C(=O)NH—(CH$_2$CH$_2$—O)$_n$—CH$_2$CH$_2$—Si(Y)$_2$O— where n is 0 to about 20;

—O—C(=O)NH—($C_1$-$C_{16}$)alkyl-NH—C(=O)O—; or

—O—C(=O)NH—(CH$_2$CH$_2$—O)$_n$—CH$_2$CH$_2$—NH—C(=O)O— where n is 0 to about 20; where each Y is independently —OH, —O-alkyl, or alkyl; and the dashed lines in Formula I represent two optional locations of crosslinking. However, the locations of the two dashed lines in Formula I are common locations of crosslinking groups because the $R^1$ groups on primary carbons are slightly more reactive to the pendant groups that are typically present on the polysaccharide prior to crosslinking. Crosslinking can occur between the two optional $R^1$ groups as illustrated in Formula I but crosslinking also typically occurs at several different $R^1$ locations across a given polymer or group of polymers. Accordingly, the crosslinking can be both intra-chain as well as inter-chain, both of which increase the viscosity of a resulting crosslinked formulation.

The Y groups can be —OH, —O-alkyl, or alkyl, or a combination thereof, depending on the specific crosslinking agent or agents used in the formulation. For example, crosslinking groups having chlorosilane groups provide Y groups that are alkyl groups, such as ($C_1$-$C_3$)alkyl groups, including methyl, ethyl, and propyl, and crosslinking groups having trialkoxysilane groups provide Y groups that are —OH or —O-alkyl groups or combinations thereof, wherein the —O-alkyl groups can be, for example, methoxy, ethoxy, propoxy, or isopropoxy.

Because the nature of the crosslinking reactions are substantially random, crosslinking can also occur between hydroxyl groups of the same polymer chain, as well as between two hydroxyl groups of the same monomer, however the crosslinking between different polymer chains occurs to a significant degree such that the organogel matrix becomes more viscous and less prone to the burst effect of many delayed release implants. Thus the crosslinked substituted polysaccharides of Formula I can be crosslinked between one or more of: a primary $R^1$ group and primary $R^1$ group on a different polysaccharide, a primary $R^1$ group and a secondary $R^1$ group on a different polysaccharide, a secondary $R^1$ group and secondary $R^1$ group on a different polysaccharide, or a primary or secondary $R^1$ group and a hydroxyl substituent on $R^1$ when $R^1$ is a substituted a ($C_2$-$C_{12}$)alkanoate on a different polysaccharide.

The groups "n" and "m" are such that each base polysaccharide of Formula I can have a molecular weight of about 10 kDa to about 1000 kDa, or about 100 kDa to about 1000 kDa, or any 100 kDa increment within said ranges. The term "base polysaccharide" refers to the polysaccharide prior to attaching pendant groups to an 'unfunctionalized' polysaccharide, which is typically a maltodextrin polymer. The molecular weights of the polysaccharides are discussed in more detail below in the section describing biodegradable polymers.

The —OSi(alkyl)$_3$ groups are hydroxyl groups protected with any suitable silyl protecting group, such as trimethylsilyl, triethylsilyl, tripropylsilyl, dimethyldecylsilyl, or any other silicon derived protecting group known to one of skill in the art (see T. W. Greene, *Protecting Groups In Organic Synthesis*; Wiley: New York, Third Edition, 1999, and references cited therein).

The invention further provides a method of delivering an active agent to a subject that includes injecting a formulation described above, for example, a formulation that includes an active agent; a non-aqueous aprotic biocompatible solvent system, wherein the solvent system comprises one or more solvents and at least one of the solvents is non-miscible with water; a plurality of hydroxyl-containing polymers, which can optionally have a base molecular weight of about 10 kDa to about 500 kDa, and which can optionally have a degree of substitution of about 0.25 to about 2, wherein the substituents can include optionally substituted ($C_2$-$C_{12}$)alkanoate groups; and a plurality of crosslinking agents, wherein the crosslinking agent comprises X—($C_1$-$C_{16}$)alkyl-X or X—($CH_2CH_2$—O)$_n$—$CH_2CH_2$—X where "n" is 0 to about 20, and each X is independently a chlorosilane group, a tri($C_1$-$C_3$)alkoxysilane group, or —NCO. The solvent system can be chemically inert with respect to the crosslinking agents, and the formulation can be substantially free of water or protic solvents. The formulation can form a gel matrix within the subject and the gel matrix becomes crosslinked when the polymers and crosslinking agents are contacted by fluids in the body of the subject. The matrix then releases the active agent, over a period of weeks, to the body of the subject, thereby delivering the active agent to the subject.

The formulations can be used for the treatment of various conditions or diseases such as cardiovascular diseases, tumors such as cancer tumors, diseases or conditions that affect the eye, and/or the formulation can be used for pain management, and the formulation can include corresponding active agents that treat such diseases. Accordingly, the formulation can be injected into any desired location of a patient. For example, the formulation can be injected into an ocular region to treat an ocular condition. Alternatively, the formulation can be injected to a site under the skin of the subject, or the formulation can be injected intramuscularly to the subject to treat other various disorders, diseases, or conditions.

In some embodiments, less than about 20 wt. %, less than about 15 wt. %, or less than 10 wt. %, of the initial mass of the active agent is delivered to the subject from the matrix within the first 10 post-injection days. The active agent can be delivered to the subject from the matrix at a rate of not more than about 10 wt. % of the initial mass of the active agent per week, after the first week post-injection. The method provides for the delivery of an effective amount of the active agent in a sustained and substantially continuous release profile, in an amount effective to treat the desired condition, such as a condition or disease recited herein.

DEFINITIONS

The invention may best be understood in view of the following definitions and descriptions.

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" means one, or in the alternative, any integer greater than one to within the practicality of the context in which the term is used. The phrase is readily understood by one of skill in the art, particularly when read in context of its usage. Typically, one or more refers to 1, 2, 3, 4, 5, 6, 7, 8, 9, or 10, or a subset thereof. For example, one or more substituents on a pendant group typically refers to one to five, or one to four, one to three, or one or two.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. For example, useful dosages can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a active agent, or an active salt or derivative thereof, required for use in treatment will vary not only with the particular agent or salt selected but also with the route of administration, the nature of the condition being treated, and the age and condition of the patient, and will be ultimately at the discretion of an attendant physician or clinician. The term "effective amount" is intended to include an amount of an active agent or formulation described herein, or a combination of actives in a formulation, e.g., that is effective to treat or prevent a disease or disorder, or to treat the symptoms of the disease or disorder, in a host. Thus, an "effective amount" generally means an amount that provides the desired effect.

The terms "treating", "treat", and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially soluble" refers to a property of a substance that dissolves completely or almost completely in a liquid material (e.g., at least 1,000 parts solute per 10,000 parts solvent). For example, a biodegradable polymer can be substantially soluble in a biocompatible solvent, such that the polymer solution in the solvent can be injected into living tissue of an organism without causing significant damage to the tissue or organism. In specific embodiments, at least about 98 wt. % of the substance completely dissolves in the liquid material at room temperature. In further specific embodiments, at least about 99 wt. % of the substance completely dissolves in the liquid material.

The term "substantially insoluble" refers to a substance that does not dissolve to any significant extent in a liquid material (e.g., 1 part solute per 10,000 parts or greater solvent). For example, an active agent can be substantially insoluble in a biocompatible solvent in which a biodegradable polymer is substantially soluble. The active agent can be suspended in the solution, e.g., in microparticulate or nanoparticulate form. In some embodiments, less than about 5 wt. % of the substance (e.g., an active agent) completely dissolves in the liquid material at room temperature. In further specific embodiments, less than about 1 wt. % of a substance completely dissolves in the liquid material. In further specific embodiments, less than about 0.1 wt. % of the substance completely dissolves in the liquid material.

The term "macromolecule" refers to an organic molecule having a molecular weight of greater than about 1000 daltons or greater than about 1200 daltons. The term can refer to natural polymers such as peptides such as LHRH, proteins, polysaccharides and nucleic acids, or it can refer to synthetic polymers such as polyesters.

The term "nucleotide" refers to a molecular entity composed of a nucleobase, sugar moiety, and phosphate group, or analogs thereof. Examples include the DNA nucleotides, i.e., adenine, guanine, cytosine, and thymidine, or the RNA nucleotide uracil, or synthetic analogs thereof. Examples of sugar moieties to which the nucleobases are covalently bonded include but are not limited to ribose and deoxyribose. Analogs of sugars can also be present; for example, halodeoxyribose analogs.

The term "biological agent" refers to a medicinally bioactive substance derived from a biological source, such as from an organism, a cell line, an isolated tissue, or the like.

The term "small molecule drug" refers to a molecular entity, often organic or organometallic, that is not a polymer that has medicinal activity. The molecular weight is often less than about 2 kDa, and is typically less than about 1 kDa. The term encompasses most medicinal compounds termed "drugs" other than protein or nucleic acids, although a small peptide or nucleic acid analog can be considered a small molecule drug. Examples include anticancer drugs, antibiotics, anti-inflammatories, and other therapeutic substances. Small molecules can be derived synthetically, semi-synthetically (i.e., from naturally occurring precursors), or biologically.

The term "complex" refers to a molecular association, which can be non-covalent, between two molecular or atomic entities. For example, certain metals bind organic groups and are referred to as complexes, such as anticancer agent cisplatin. Or, certain macromolecules such as proteins can bind small molecule ligands, the product also being termed a complex. Complexes can also form between nucleic acid molecules, such as in DNA complementary nucleotide pairing and in association of DNA with RNA via complementary nucleotide pairing. A complex formed between DNA or messenger RNA and a small interfering RNA (siRNA) is another example of complementary nucleotide pairing.

A "spray-dried protein" is a protein that has undergone a process of drying from a solution, which can be a water solution, where a relatively fine spray of the solution is subjected to conditions that serve to remove liquid (e.g., water) and provide a finely powdered form of the protein, optionally in the presence of one or more stabilizers.

Because all solvents, at least on a molecular level, will be soluble in water (i.e., miscible with water) to some very limited extent, the term "water immiscible" refers to a liquid that does not mix in all proportions with water. A water immiscible liquid can dissolve to some extent in water, but at some relative proportions of water and the liquid, phase separation occurs. In specific embodiments, for a water immiscible solvent, about 10 wt. % or less of the solvent is soluble in or is miscible with water. In another specific embodiments, for a water immiscible solvent, about 5 wt. % or less of the solvent is soluble in or is miscible with water. In another specific embodiments, for a water immiscible solvent, about 1 wt. % or less of the solvent is soluble in or is miscible with water. For the purposes of this disclosure, solubility values of solvent in water are considered to be determined at 20° C. Because it is generally recognized that solubility values as reported may not always be conducted at the same conditions, solubility limits described herein as percent by weight miscible or soluble with water as part of a range or upper limit may not be absolute.

The term "miscible to dispersible in aqueous medium or body fluid" refers to a substance or mixture that interacts with aqueous medium, i.e., a liquid containing water, or with body fluid, e.g., blood, intercellular fluid, or the like, such that the solubility of the substance or mixture is either complete (miscible) or partially soluble (dispersible) in the fluid.

The term "immiscible to insoluble in aqueous medium or body fluid" refers to a substance or mixture that does not dissolve to any significant extent in aqueous media or body fluids.

The term "ambient and physiological temperature" refers to the temperature range of about 15° C. to about 40° C. (e.g., 33.2-38.2° C. in normal and relatively healthy humans).

The term "miscible to dispersible in aqueous medium or bodily fluids" refers to a substance or mixture that either completely dissolves or uniformly distributes throughout an aqueous medium or body fluid.

The term "immiscible to non-dispersible in aqueous medium or bodily fluids" refers to a substance or mixture that does completely dissolves or uniformly distribute throughout an aqueous medium or body fluid.

The term "dissipation into body fluid upon placement within a body tissue" refers to a substance that when a quantity is emplaced within body tissue dissolves or disperses away from the original site of emplacement.

The term "diffusion into body fluid upon placement within a body tissue" refers to a substance that when a quantity is emplaced within body tissue dissolves or disperses in body fluid such that it is transported in the body fluid from the original site of emplacement.

The term "absorption into body fluid upon placement within a body tissue" refers to a substance that when a quantity is emplaced within body tissue is taken up by body fluid such that it is transported in the body fluid from the original site of emplacement.

The term "degradation in body fluid upon placement within a body tissue" refers to a substance that when a quantity is emplaced within body tissue is chemically broken down in body fluid such that its chemical nature is altered.

The term "non-aqueous" refers to an absence of water. For instance, a non-aqueous liquid is a liquid that is substantially free of water, e.g., includes less that about 1 wt. % water.

The term "biodegradable" refers to a substance that is acted on by agents within living tissue such as enzymes to alter the chemical nature of the substance. For example, a biodegradable polymer can be broken down by tissue enzymes into components of low molecular weight such as monomeric fragments.

The term "hydrophobic" refers to a substance, molecule, or a domain of a substance of molecule that does not dissolve or is not wetted by water. The energetic interaction between a hydrophobic substance, molecule, or domain is unfavorable. Examples include solvents such as hydrocarbons and esters that when mixed with water undergo phase separation.

The term "substantially insoluble in the biocompatible solvent system" refers to a substance or mixture that does not dissolve to any significant degree in a solvent or mixture of solvents that are biocompatible, as defined above. In specific embodiments, less than about 5 wt. % of the substance or mixture (e.g., active agent) completely dissolves in the biocompatible solvent system. In further specific embodiments, less than about 1 wt. % of the substance or mixture completely dissolves in the biocompatible solvent system. In further specific embodiments, less than about 0.1 wt. % of the substance or mixture completely dissolves in the biocompatible solvent system.

The term "substantially insoluble in water or bodily fluids" refers to a substance or mixture that does not dissolve to any significant degree in water or in body fluids such as blood, intercellular fluid, or the like. In specific embodiments, less than about 5 wt. % of the substance or mixture (e.g., active agent) completely dissolves in water or in body fluids. In further specific embodiments, less than about 1 wt. % of the substance or mixture completely dissolves in water or in body fluids. In further specific embodiments, less than about 0.1 wt. % of the substance or mixture completely dissolves in water or in body fluids.

The term "pendent group" refers to a chemical moiety or group that is covalently bonded to a polymer backbone, but is not itself part of the backbone or continuous molecular chain.

The term "glucopyranose unit" refers to a glucopyranose moiety contained within a polymeric structure. In specific embodiments, the glucopyranose units can be linked by $\alpha(1\rightarrow4)$ glycosidic bonds. In other specific embodiments, some glucopyranose units can be linked by $\alpha(1\rightarrow6)$ glycosidic bonds.

The term "polysaccharide" refers to a polymer of monosaccharide units. Examples include starch, amylase, maltodextrin, and derivatives thereof.

The term "substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Pendant groups can be optionally substituted with one or more (e.g., 1-6) of a variety of indicated groups. Suitable indicated groups include, for example, alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, acyloxy, alkoxycarbonyl, amino, imino, alkylamino, acylamino, silyl ether, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NRxRy and/or COORx, wherein each Rx and Ry are independently H, alkyl, alkenyl, aryl, heteroaryl, heterocycle, cycloalkyl or hydroxy. When a substituent is keto (i.e., =O) or thioxo (i.e., =S) group, then 2 hydrogens on the substituted atom are replaced.

The term "degree of substitution" refers the numerical average of the number of substituents or pendant groups per monomeric unit of the base polymer.

The term "suspension" or "dispersion" refers to a mixture of particles of a solid within a liquid, the particles being the dispersed phase, while the suspending medium is the continuous phase. The suspension can be a mixture of fine, nonsettling particles of a solid within a liquid. With a suspension, the particles are typically distributed through the liquid. With a suspension, the particles are typically not dissolved (i.e., are undissolved or unsolubilized) to a significant degree. The particles can be in microparticulate or nanoparticulate form. Additionally, the suspension can be a homogeneous suspension.

The term "homogeneous suspension" or "homogeneous dispersion" refers to a suspension or dispersion in which the particles are uniformly or essentially uniformly distributed through the liquid or solid, for example, at a macroscopic level.

The term "average particle size" refers to, in a population of particles, a numerical value representing the average diameter or major dimension of the population, or the average particle size can refer to the size where 50% of the particles are equal or smaller in diameter than the diameter of the largest fraction of the particle population (i.e., the $D_{50}$ value).

The term "inert" and "little or no chemical interaction" refers to a situation wherein at least two molecular entities are in intimate contact but no reaction proceeds therebetween at any appreciable rate.

The term "mammal" refers to an organism of the order Mammalia, including humans, primates, and non-primates such as dogs, cats, horses, cattle, marsupials, monotremes, and the like.

The term "locally delivered" refers to a mode of delivery of a pharmaceutical substance from an implanted structure or depot to tissues predominantly in the vicinity of the implant within the organism. The pharmaceutical substance is delivered to a localized site in the subject but is not detectable at a biologically-significant level in the blood plasma of the subject.

The term "systemically delivered" refers to a mode of delivery of a pharmaceutical substance from an implanted structure or depot to tissues throughout the organism. The pharmaceutical substance is detectable at a biologically-significant level in the blood plasma of the subject.

The term "burst" refers to the release rate of an active agent over time from an implant where the initial release rate is not uniform and is substantially greater during the initial time period immediately following emplacement of the implant the tissue of a patient.

The crosslinkable formulations described herein can be particularly suitable for delivery of an active agent to an ocular region or an ocular site to treat an ocular condition in a delayed release manner.

An "ocular region" or "ocular site" refers generally to any area of the eyeball, including the anterior and posterior segment of the eye, and which generally includes, but is hot limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

An "ocular condition" is a disease, ailment, or condition that affects or involves the eye or one of the parts or regions of the eye. Broadly speaking, the eye includes the eyeball and the tissues and fluids which constitute the eyeball, the periocular muscles (such as the oblique and rectus muscles), and the portion of the optic nerve which is within or adjacent to the eyeball.

An anterior ocular condition is a disease, ailment, or condition which affects or which involves an anterior (i.e. front of the eye) ocular region or site, such as a periocular muscle, an eye lid, or an eye ball tissue or fluid which is located anterior to the posterior wall of the lens capsule or ciliary muscles. Thus, an anterior ocular condition primarily affects or involves the conjunctiva, the cornea, the anterior chamber, the iris; the posterior chamber (behind the iris, but in front of the posterior wall of the lens capsule), the lens or the lens capsule, and blood vessels and nerve which vascularize or innervate an anterior ocular region or site.

Thus, an anterior ocular condition can include a disease, ailment or condition, such as for example, aphakia; pseudophakia; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders; and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment, or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment, or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

Biocompatible Solvent System

The term "biocompatible solvent" refers to a liquid material that can be emplaced within living tissue of an organism without causing significant damage to the tissue or organism. The biocompatible solvent system can be a single solvent or it can include two or more (e.g., 2, 3 or 4) solvents. The solvent system is used to solubilize or dissolve the biodegradable polymer, for example, a maltodextrin that includes pendant groups. Any suitable solvent system can be employed, provided the biodegradable polymer is substantially soluble in at least one solvent of the solvent system, provided the solvent system is non-aqueous and aprotic, and provided the solvent system does not react with the crosslinking agent of the formulation (e.g., the solvent system is chemically inert with respect to the crosslinking agent). In some embodiments, the biodegradable polymer of the formulation will be soluble in the solvent system, but the active agent will be substantially insoluble. In some embodiments, at least one component of the solvent system is not water miscible.

The term "aprotic solvent" refers to a liquid that does not include an exchangeable proton. Exchangeable protons include hydroxyl groups, accordingly aprotic solvents do not include water, alcohols, or carboxylic acids. Examples of aprotic solvents include hydrocarbons, amides such as dimethylformamide, esters such as ethyl acetate, sulfoxides such as dimethylsulfoxide, and the like.

The overall solvent system will typically be immiscible with water. Water miscibility can be determined experimentally as follows: Water (1-5 g) is placed in a tared clear container at a controlled temperature (e.g., at about 20° C.). The container and the water is weighed, and a candidate solvent is then added dropwise. The solution is swirled to observe phase separation, should it occur. When the saturation point appears to be reached, as determined by observation of phase separation, the solution is allowed to stand overnight and is re-checked the following day. If the solution is still saturated, as determined by observation of phase separation, then the percent (w/w) of solvent added is determined. Otherwise more solvent is added and the process is repeated. Solubility or miscibility is determined by dividing the total weight of solvent added by the final weight of the solvent/water mixture. When solvent mixtures are used, for example 20% triacetin and 80% benzyl benzoate, they are pre-mixed prior to adding to the water.

The solvent system can include at least one organic solvent that is miscible to dispersible in aqueous medium or body fluid. Alternatively, the solvent system can include at least one organic solvent that is immiscible to insoluble in aqueous medium or body fluid. Alternatively, the solvent system can include a combination of at least one organic solvent that is miscible to dispersible in aqueous medium or body fluid, and at least one organic solvent that is immiscible to insoluble in aqueous medium or body fluid. Alternatively, the solvent system can include a combination of at least one organic solvent that is miscible to dispersible in aqueous medium or body fluid, and at least one organic solvent that is immiscible to insoluble in aqueous medium or body fluid, wherein the polymer has greater solubility in the miscible to dispersible solvent, as compared to the immiscible to insoluble solvent.

Classes of solvents suitable for use in the solvent system include, for example, alkyl esters, aryl esters, diesters, triesters, or a combination thereof. Suitable specific solvents include, for example, ethyl heptanoate, ethyl octanoate, benzyl benzoate, glycerol triacetate (triacetin), glycerol tributyrate, glycerol trioctanoate, dimethyl isosorbide, N-methyl-2-pyrrolidone (NMP), dimethyl sulfoxide (DMSO), dimethylformamide (DMF), dimethylacetamide (DMAC), or a combination thereof.

In one embodiment, the solvent system includes at least one aliphatic ester. In some embodiments, the solvent system can include one or more aliphatic esters, such as glyceryl triacetate, glyceryl tributyrate, or a $(C_1\text{-}C_4)$alkyl$(C_2\text{-}C_{12})$alkanoate, for example, ethyl heptanoate or butyl hexanoate. The solvent system can also include one or more aromatic esters; such as benzyl benzoate. The solvent system can include combinations of any of these solvents as well, such as in ratios of about 1:10 to about 10:1, and any integer ratio in between. Additional biocompatible aprotic solvents for use in the solvent system are commercially available from Sigma-Aldrich (see *The Aldrich Handbook of Fine Chemicals and Laboratory Equipment*, Milwaukee, Wis. (2009)). The biocompatible solvent system can be selected such that it is able to diffuse into bodily fluids, so that the injected formulation effectively coagulates and/or gels in vivo.

The solvent system can be present in any suitable and effective amount, provided the biodegradable polymer is substantially soluble in the solvent system. The type and amount of solvent present in the formulation can depend upon the desired properties of the controlled release implant because the type and amount of solvent can influence the length of time in which the active agent is released from the controlled release implant.

The solvent system is typically about 10 wt. % to about 90 wt. % of the formulation. In one embodiment, the solvent system is present in about 10 wt. % to about 40 wt. % of the formulation. In another embodiment, the solvent system is present in about 40 wt. % to about 90 wt. % of the formulation. In another embodiment, the solvent system is present in about 30 wt. % to about 80 wt. % of the formulation. In some embodiments, the solvent system is present in about 30-40 wt. %, 40-50 wt.%, 50-60 wt. %, 60-70 wt. %, or 70-80 wt. % of the formulation.

Biodegradable Polymers

The term "biodegradable polymer" refers to a polymeric material, as is well known in the art, that when placed or implanted within living tissue of an organism undergoes chemical breakdown. The biodegradable polymers used in the formulations described herein can include any biodegradable polymer that is substituted by two or more hydroxyl groups. In some embodiments, the biodegradable polymer can have 2 to about 200 total hydroxyl groups, and in other embodiments, the biodegradable polymer can have one to about four hydroxyl groups per monomer. In some embodiments, the biodegradable polymer can have one to three hydroxyl groups per monomer. Examples of suitable biodegradable polymers include polysaccharides, polyglycerol, esterified polyglycerol, comb-shaped PLAs, star-shaped PLAs, and/or PEG/PLAs, PEG-PLA block copolymers, or polyvinylacetate (PVA), where the polymers include a sufficient amount of hydroxyl groups (e.g., two or more) such that the viscosity of a formulation increases upon crosslinking.

The biodegradable polymers of the formulation described herein can include a single type of polymer, or it can include two or more types of biodegradable polymers. These polymers act as gelling agents and aid in the formation of an implant in vivo. The polymers are typically substantially soluble in the biocompatible solvent system. For example, the biodegradable polymer can have a solubility of at least about 50 g/L in the biocompatible solvent system (e.g., at 25° C. and 1 atm).

Examples of suitable biodegradable polymers include, but are not limited to, polysaccharides and copolymers that include polysaccharides. The polymer can also be any polymer with a sufficient amount of free hydroxyl groups such that the polymer can be crosslinked to increase the viscosity of a formulation, compared to a corresponding non-crosslinked formulation. In one embodiment, the biodegradable polymers include polysaccharides. In another embodiment, the biodegradable polymer can include substituted polysaccharides.

In one embodiment, the biodegradable polymer has a viscosity of at least about 100 cP at 37° C. when dissolved in the solvent system of choice. In other embodiments, the biodegradable polymer has a viscosity of about 1,000 cP to about 30,000 cp at 37° C., about 5,000 cP to about 25,000 cp at 37° C., or about 10,000 cP to about 20,000 cp at 37° C.

In one embodiment, the biodegradable polymer is present in about 2 wt. % to about 50 wt. % of the formulation. In another embodiment, the biodegradable polymer is present in about 5 wt. % to about 50 wt. %, about 10 wt. % to about 40 wt. %, about 2 wt. % to about 30 wt. %, about 20 wt. % to about 30 wt. %, about 2 wt. % to about 10 wt. % of the formulation, or about 2 wt. %, about 3 wt. %, about 5 wt. %, about 7 wt. %, about 10 wt. %, about 12 wt. %, about 15 wt. %, or about 20 wt. % of the formulation.

Hydrophobic Polysaccharides

Biodegradable polymers that can be used in the formulations described herein include various hydrophobic polysaccharides derived from natural biodegradable polysaccharides. The term "hydrophobic derivative of a natural biodegradable polysaccharide" refers to a natural biodegradable polysaccharide having one or more hydrophobic pendent groups attached to the polysaccharide, typically through the free hydroxyl groups of the natural polysaccharide. In many cases the hydrophobic derivative includes a plurality of groups that include hydrocarbon segments attached to the polysaccharide. When a plurality of groups, such as hydrocarbon segments, is attached to a polysaccharide, the pendant hydrocarbon segments are collectively referred to as the "hydrophobic portion" of the hydrophobic derivative. The hydrophobic derivatives therefore include a hydrophobic portion and a polysaccharide (backbone) portion.

The polysaccharide portion can be a natural biodegradable polysaccharide, including polysaccharides and/or polysaccharide derivatives that are obtained from natural sources, such as plants or animals. Natural biodegradable polysaccharides include any polysaccharide that has been processed or modified from a natural biodegradable polysaccharide (for example, maltodextrin processed from starch). Examples of biodegradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Some specific polysaccharides include low molecular weight polymers that have little or no branching, such as those that are derived from and/or found in starch preparations, for example, maltodextrin, amylose, and cyclodextrin. Accordingly, the natural biodegradable polysaccharide can be a substantially non-branched or a completely non-branched poly(glucopyranose) polymer.

"Amylose" refers to a linear polymer having repeating glucopyranose units that are joined by α-1,4 linkages. Some amylose polymers can have a small amount of branching by α-1,6 linkages (typically less than about 0.5%) but still demonstrate the same physical properties as linear (unbranched) amylose polymers. Amylose polymers derived from plant sources typically have molecular weights of about $1 \times 10^6$ Da or less. Amylopectin, comparatively, is a branched polymer having repeating glucopyranose units that are joined by α-1,4 linkages to form linear portions, and several linear portions are linked together via α-1,6 linkages. The branch point linkages are generally greater than 1% of the total linkages and typically 4%-5% of the total linkages. Generally, amylopectin derived from plant sources have molecular weights of $1 \times 10^7$ Da or greater.

In some embodiments of the invention, starch can be used in the preparation of a hydrophobic derivative of amylose. The starch can be purified amylose, synthetically prepared amylose, an enriched amylose preparation, or a preparation having a high amylose content. In many starch sources, amylose is present along with the branched polysaccharide amylopectin. If a mixture of amylose and a higher molecular weight precursor is used (such as amylopectin), amylose can be present in the composition in an amount greater than the higher molecular weight precursor. For example, starch preparations having high amylose content, purified amylose, synthetically prepared amylose, or enriched amylose preparations can be used to prepare a hydrophobic derivative of an amylose polymer.

In some embodiments the composition includes a mixture of polysaccharides including amylose where the amylose content in the mixture of polysaccharides is 50% or greater, 60% or greater, 70% or greater, 80% or greater, or 85% or greater, by weight. In other embodiments the composition includes a mixture of polysaccharides including amylose and amylopectin where the amylopectin content in the mixture of polysaccharides is 30% or less, 15% or less, or 10% or less. The amount of amylopectin present in a starch may be reduced by treating the starch with amylopectinase, which cleaves the amylopectin α-1,6 linkages, resulting in the debranching of amylopectin to provide amylose.

Amylose of particular molecular weights can be obtained commercially or they can be prepared. For example, synthetic amyloses with average molecular masses of 70 kDa, 110 kDa, and 320 kDa, can be obtained from Nakano Vinegar Co., Ltd. (Aichi, Japan). A selection of a particular size range of amylose may depend on factors such as the desired physical characteristics of the composition (e.g., viscosity), the desired rate of degradation of the implant, and the nature and amount of the active agent. Purified or enriched amylose preparations can be obtained commercially, or they can be prepared using standard biochemical techniques such as chromatography. High-amylose cornstarch can be used to prepare the hydrophobic derivative.

Maltodextrin is typically generated by hydrolyzing a starch slurry with heat-stable α-amylase at about 85-90° C. until the desired degree of hydrolysis is reached, followed by inactivating the α-amylase by a second heat treatment. The maltodextrin can be purified by filtration and then spray dried to a final product. Maltodextrins are typically characterized by their dextrose equivalent (DE) value, which is related to the degree of hydrolysis, and is defined as: DE=MW dextrose/number–averaged MW starch hydrosylate×100. Maltodextrin is considered to have a molecular weight less than amylose.

A starch preparation that has been totally hydrolyzed to dextrose (glucose) has a DE of 100, whereas starch has a DE of about zero. A DE of greater than 0 but less than 100 characterizes the mean-average molecular weight of a starch hhydrosylate, and maltodextrins are considered to have a DE of less than 20. Maltodextrins of various molecular weights, including those in the range of about 500 Da to 5000 Da, are commercially available (for example, from CarboMer, San Diego Calif.).

The polysaccharides used in the formulation can also be natural biodegradable non-reducing polysaccharides. A non-reducing polysaccharide can provide an inert matrix thereby improving the stability of the active agent, such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and/or sucrose (β-D-fructofuranosyl α-D-glucopyranoside). One non-reducing polysaccharide is polyalditol, which is available from GPC (Muscatine, Iowa). The polysaccharide can also be a glucopyranosyl polymer, such as a polymer that includes repeating (1→3)O-β-D-glucopyranosyl units.

Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by *Leuconostoc mesenteroides* B512F. Dextran can be obtained in low molecular weight preparations. Enzymes (dextranases) from molds, such as *Penicillium* and *Verticillium*, have been shown to degrade dextran. Many bacteria can also produce extracellular dextranases that split dextran into low molecular weight sugars.

In some embodiments, the polysaccharide of the formulation can include chondroitin sulfate (repeating disaccharide units of D-galactosamine and D-glucuronic acid) or hyaluronic acid (alternating β-1,4-glucuronic acid and β-1,3-N-acetyl-D-glucosamine units).

When a polysaccharide of the formulation is substituted with pendant groups, for example, hexanoate groups to a DS of about 1.6, the hydrophobic derivative becomes insoluble in water. Insolubility is a standard term of art, referring to 1 part solute per 10,000 parts or greater solvent (see *Remington: The Science and Practice of Pharmacy*, 20th ed. (2000), Lippincott Williams & Wilkins, Baltimore Md.).

Hydrophobic derivatives of the natural biodegradable polysaccharides can have an average molecular weight of up to about 1,000,000 Da, up to about 300,000 Da, or up to about 100,000 Da. Use of these molecular weight derivatives can provide implants with desirable physical and drug-releasing properties. In some aspects the hydrophobic derivatives have a molecular weight of about 500,000 Da or less, about 250,000 Da or less, about 100,000 Da or less, about 50,000 Da or less, or 25,000 Da or less. Some specific polysaccharide size ranges include about 2,000 Da to about 500,000 Da, about 40,000 Da to about 160,000 Da, about 2,000 Da to about 20,000 Da, or about 4,000 Da to about 10,000 Da.

The molecular weight of the polymer can be more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers have relatively high molecular weight and such minor variations do not affect the overall properties of the polymer preparation. The $M_w$ can be measured using common techniques, such as light scattering or ultracentrifugation. $M_w$ and other terms used to define the molecular weight of polymer preparations are discussed by Allcock and Lampe, *Contemporary Polymer Chemistry* (1990); pg 271.

The addition of hydrophobic pendant groups to a polymer causes an increase in molecular weight of the polysaccharide from its underivitized (base) starting molecular weight. In some aspects, the addition of hydrophobic portion causes an increase in molecular weight of the polysaccharide of about 20% or more, about 50% or more, about 75% or more, about 100% or more, or about 125% or more, compared to the base form of the polysaccharide.

As an example, a maltodextrin having a starting weight of about 3000 Da can be derivitized to provide pendent hexanoate groups coupled to the polysaccharide by ester linkages, to provide a degree of substitution (DS) of about 2.5. This provides a hydrophobic polysaccharide having a theoretical molecular weight of about 8400 Da, which corresponds to an increase of about 280%.

In forming the hydrophobic derivative of the polysaccharide, a compound having a hydrocarbon segment can be covalently coupled to one or more portions of the polysaccharide, for example, free hydroxyl groups of the monomer units. This provides a polysaccharide derivative with one or more pendent groups. Each pendent group includes a hydrocarbon segment that can constitute all of the pendent chemical group, or merely a portion of the pendent group. In some embodiments, the hydrophobic polysaccharide can include Formula A:

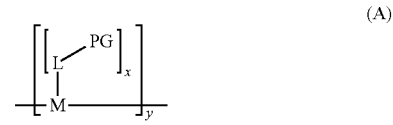

(A)

where each M is independently a monosaccharide unit, each L is independently a linking group or a direct bond, each PG is independently a pendent group, each x is independently 0 to about 3. When x is 0, the bond between L and M is absent. The variable y is about 3 or more.

For the compounds of Formula A, the monosaccharide unit (M) can be, for example, D-glucopyranose (e.g., α-D-glucopyranose). Additionally, the monosaccharide unit (M) can include poly-α(1→4) glucopyranose, poly-α(1→6) glucopyranose, or a mixture or combination of both poly-α(1→4) glucopyranose and poly-α(1→6) glucopyranose. For example, the monosaccharide unit (M) can include glucopyranose units, wherein at least about 90% are linked by α(1→4) glycosidic bonds. The polysaccharide can include up to about 5,000 monosaccharide units (i.e., y in Formula A can be up to 5,000. In some embodiments, the variable y in Formula A can be about 3 to about 5,000, about 3 to about 4,000, or about 100 to about 4,000.

A "pendant group" (PG) refers to a group of covalently bonded carbon atoms having the formula $(CH_n)_m$, wherein m is 2 or more, and n is independently 2 or 1, and n is 3 at the terminal carbon if that carbon is unsubstituted. A hydrocarbon segment can include saturated hydrocarbon groups or unsaturated hydrocarbon groups. Examples include alkyl, alkenyl, alkynyl, cyclic alkyl, cyclic alkenyl, aromatic hydrocarbon and arylalkyl (e.g., benzyl or phenethyl) groups. The pendant group can include linear, straight chain or branched $C_1$-$C_{20}$ alkyl groups, an amine terminated hydrocarbon, or a hydroxyl terminated hydrocarbon.

Linking groups (L) that can be used to connect the pendent groups to the base polysaccharide include carboxylic esters, carbonate, borates, silyl ethers, disulfide groups, and hydrazone groups. In some cases, hydroxyl groups can be reacted with groups such as isocyanate and epoxy to form the pendent groups on the base polysaccharide.

Synthesis of the polysaccharide derivatives can be carried out to provide a desired number of pendant groups on the base polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group): 1 (polysaccharide monomer) by weight.

The weight ratio of glucopyranose units to pendent groups can vary, but will typically be about 1:1 to about 100:1. Specifically, the weight ratio can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-3 or about 0.5-2. In some embodiments, the polysaccharides will have a degree of substitution of about 0.25 to about 2, about 0.5 to about 2; about 0.5 to about 1.5, or about 0.2 to about 2.7. In many embodiments, a polysaccharide with a DS of less than 0.5 is not soluble in many solvent systems typically used for the formulations.

In some embodiments, very low molecular weight (less than 10,000 Da) glucopyranose polymers are reacted with compounds having the hydrocarbon segment to provide low molecular weight hydrophobic glucopyranose polymers. In one example, a maltodextrin (10 g, m.w. 3000-5000 Da; ~3 mmols) is dissolved in a suitable solvent, such as DMSO, tetrahydrofuran, or a combination thereof. Butyric anhydride (18 g, 0.11 mol) is then added to the maltodextrin solution. The reaction is allowed to proceed, effectively forming pendent butyrate groups on the pyranose rings of the maltodextrin. This results in a degree of substitution (DS) by butyrate group on the maltodextrin of about 1.

For maltodextrin and other polysaccharides that can include three hydroxyl groups per monomeric unit, on average, one of the three hydroxyl groups per glycopyranose monomeric unit will typically be substituted with a pendant group, such as a butyrate group or a hexanoate group. A maltodextrin polymer having this level of substitution is referred to herein as maltodextrin-butyrate DS1, or MD-Bu DS1. DS refers to the average number of reactive groups (including hydroxyl and other reactive groups) per monomeric unit that are substituted with pendent groups.

An increase in the DS can be achieved by incrementally increasing the amount of compound that provides the pendant group. For example, butyrylated maltodextrin having a DS of 2.5 can be prepared by reacting 10 g of maltodextrin (m.w. 3000-5000 Da; ~3 mmols) with 0.32 mols butyric anhydride.

High DS polysaccharide are generally more hydrophobic and therefore can be more resistant to degradation in the body. For example, an implant formed from maltodextrin-butyrate DS1 has a rate of degradation that is faster than an implant formed from maltodextrin-butyrate DS2. The type of hydrocarbon segment present in the pendent groups can also influence the hydrophobic properties of the polymer. A hydrophobic polymer can be prepared by the reaction of maltodextrin with valproic acid/anhydride with maltodextrin (MD-val). The reaction can be carried out to provide a relatively lower degree of substitution of the hydroxyl groups, such as is in the range of 0.5-1.5, while maintaining the same quality of hydrophobicity as MD-Bu DS1. Although these polysaccharides have a lower degree of substitution, the short chain branched alkyl group imparts considerable hydrophobic properties to the polysaccharide.

In some embodiments, the pendent group can be a hydrocarbon segment that is a linear, branched, or cyclic $C_2$-$C_{18}$ group. In other embodiments, the hydrocarbon segment can be a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond, and the pendant group can be substituted by one or more hydroxyl groups or amino groups, which may participate in reacting with the crosslinking groups of the formulation.

Examples of compounds that can be used to form pendant groups include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide by an ester group. The hydroxyl group of a polysaccharide can also cause ring opening of lactones to provide pendent open-chain hydroxy esters. Exemplary lactones that can be reacted with the polysaccharide include caprolactone and glycolides.

Generally, if compounds having large hydrocarbon segments are used for the synthesis of the hydrophobic derivative, a smaller amount of the compound may be needed for its synthesis. For example, as a general rule, if a compound having a hydrocarbon segments with an alkyl chain length of $C_x$ is used to prepare a hydrophobic derivative with a DS of 1, a compound having a hydrocarbon segment with an alkyl chain length of $C_{(x \times 2)}$ is reacted in an amount to provide a hydrophobic derivative with a DS of 0.5.

The hydrophobic derivative of the biodegradable polysaccharide can also be synthesized having combinations of pendent groups with two or more different hydrocarbon segments. For example, the hydrophobic derivative can be synthesized using compounds having hydrocarbon segments with different alkyl chain lengths. In one mode of practice, a polysaccharide is reacted with a mixture of two or more fatty acids (or derivatives thereof). The fatty acids can be one or more of acetic acid, propionic acid, butyric acid, isobutyric acid, valeric acid, caproic acid, caprylic acid, capric acid, and lauric acid, or their respective anhydrides, to generate the hydrophobic derivative.

In some embodiments, the substituted polysaccharides have a solubility of at least about 10 mg/mL in the biocompatible solvent system. In other embodiments, the substituted polysaccharides have a solubility of at least about 15 mg/mL, at least about 20 mg/mL, at least about 25 mg/mL, at least about 50 mg/mL, or at least about 100 mg/mL, in the biocompatible solvent system.

Additional features and descriptions of biodegradable polysaccharides can be found in U.S. Patent Publication Nos. 2007/0218102, 2007/0260054, and 2007/0224247, and references cited therein.

Linking Group

A pendant group (PG) can optionally be linked to a monosaccharide unit (M) through a linker or linking group (L). A pendant group can independently be absent or present on each of the monosaccharide units (M) of the polymer. When more than one pendant group is present on polymer, such as a polysaccharide, each of the pendant groups can be the same or they can be different than other pendant groups on the polymer.

The reactive functional groups present on the pendant group and a monosaccharide unit (M) can influence the requisite functional groups to be present on the linking group (L). The nature of the linking group is not critical, provided the pendant group employed possesses acceptable mechanical properties and release kinetics for the selected therapeutic application. The linking group (L) is typically a divalent organic radical having a molecular weight of from about 25 daltons to about 400 daltons. More specifically, the linking group can have a molecular weight of from about 40 daltons to about 200 daltons. By combining the hydroxyl group of the polymer and the pendant group's starting material, the linkage formed can be an ester, an amide, a thioester, a phosphoric acid ester, a sulphonic acid ester, a carbonate, a borate, or a silyl ether.

In some embodiments, the linking group (L) can be a divalent, branched or unbranched, saturated or unsaturated, hydrocarbon chain, having from 1 to about 20 carbon atoms, where one or more (e.g. 1, 2, 3, or 4) of the carbon atoms is optionally interrupted with one or more oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), oxycarbonyl (—OC(=O)—), imine (—C=NH—), sulfinyl (—SO—), sulfonyl (—SO$_2$—) or (—NR—) groups, wherein R is H, alkyl, cycloalkyl alkyl, or aryl alkyl.

The linking group (L) can be formed by the reaction of a hydroxyl group of a polymer and a reactive group of a group that will become a pendant group. Examples of hydroxyl-reactive groups include acetal, carboxyl, anhydride, acid halide, and the like. These groups can be used to form a hydrolytically-cleavable covalent bond between, for example, a hydrophobic group and/or a silyl ether group and a glucopyranose unit of the polysaccharide backbone. In some embodiments, the pendant group-substituted hydrophobic polysaccharide can include chemical linkages that are both enzymatically cleavable (e.g., in the polymer backbone) and non-enzymatically hydrolytically cleavable (e.g., in the linkage between either, or both, a pendent hydrophobic group and/or a pendent silyl ether group).

The hydrocarbon chain of the linking group (L) can optionally be substituted on carbon with one or more (e.g. 1, 2, 3, or 4) substituents selected from alkyl, alkenyl, alkoxy, halo, haloalkyl, hydroxy, hydroxyalkyl, aryl, cycloalkyl, alkanoyl, alkoxycarbonyl, amino, alkylamino, acylamino, nitro, trifluoromethyl, trifluoromethoxy, carboxy, carboxyalkyl, keto, cyano, acetamido, acetoxy, acetyl, benzoyl, benzoylamino, benzoyloxy, benzyl, benzyloxy, benzyloxycarbonyl, carbamoyl, isocyannato, NR$^x$R$^y$ and/or COOR$^x$, wherein each R$^x$ and R$^y$ are independently H, alkyl, alkenyl, aryl, heteroaryl, heterocycle, cycloalkyl or hydroxy.

Active Agents and Diseases

The terms "active pharmaceutical ingredient (API)" and "active agent" refer to a therapeutic, medicinal substance, such as is commonly termed a "drug" or a "medicament" suitable for administration for medical treatment of a malcondition in a living organism, such as a human. The active agent can be any therapeutic agent that can be delivered to a patient using the crosslinkable formulation. Examples of active agents include macromolecules, proteins, peptides, genes, polynucleotides or analogues or complexes thereof, nucleotides, biological agents, and small molecule drugs, as well as PEGylated proteins, PEGylated aptamers, enzymes, blood clotting factors, growth factors, cytokines, hormones, and vaccines.

The active agent can be present in the formulation in any suitable and appropriate amount, provided that upon administration of the formulation, a safe and therapeutically effective amount of active agent is delivered. Thus, the active agent can be present in the formulation in about 0.1 wt. % to about 30 wt. % of the formulation, or in about 1 wt. % to about 10 wt. % of the formulation. Accordingly, the active agent can therefore be present in the formulation in about 0.1 wt. %, about 0.25 wt. %, about 0.5 wt. %, about 1 wt. %, about 2 wt. %, about 3 wt. %, about 5 wt. %, about 7.5 wt. %, about 10 wt. %, about 12 wt. %, about 15 wt. %, about 20 wt. %, about 25 wt. %, or about 30 wt. %.

In some embodiments, the active agent is in the form of a spray-dried protein. Active agent compositions can include stabilizing factors, such as monosaccharides, disaccharides (e.g., trehalose), or trisaccharides for spray-dried proteins, or a polysaccharides for nucleotides.

The active pharmaceutical ingredient (API) or "active agent" can be soluble in the biocompatible solvent system, or it can be substantially or completely insoluble in the solvent system. When insoluble, the active agent will be undissolved, unsolubilized and/or suspended in the formulation. Thus, in some embodiments, the active agent will be dissolved in the solvent system, and in other embodiments, the active agent will be dispersed in the solvent system, for example, as particles, preferably between about 0.5 to 100 microns in diameter, or from about 1 to about 20 microns in diameter, for example, for a spray dried protein. For example, where the active agent is dispersed in the formulation, the active agent can be in the form of particles having an average particle size of less than about 20 microns.

In some embodiments, the active agent can have a solubility of less than about 10 g/L in the biocompatible solvent system, at 25° C. and 1 atm. The active agent can also have a solubility of less than about 1 g/L, less than about 500 mg/L, less than about 250 mg/L, less than about 100 mg/L, less than about 50 mg/L, or less than about 10 mg/L, in the biocompatible solvent system, at 25° C. and 1 atm.

The solubility of the active agent can be measured in water as well. For example, the active agent can have a water solubility of greater than about 500 mg/L, greater than about 1 g/L, greater than about 5 g/L, greater than about 10 g/L, greater than about 20 g/L, greater than about 25 g/L, greater than about 50 g/L, greater than about 100 g/L, or greater than about 250 g/L at 25° C. and 1 atm. In some embodiments, the active agent is hydrophilic, and thus very water soluble.

Suitable specific active agents include, for example, those active agents illustrated in Table A below. Additional suitable active agents include, for example, those active agents recited in the *Physician's Desk Reference*, 64$^{th}$ Edition (2010). It is appreciated that those skilled in the art of pharmaceutical chemistry understand that when a proprietary name is provided as active agents in Table A below, the specific active agent is the drug contained in the recited formulation.

TABLE A

Ophthalmic Disease Indications and Active Agents

| Disease Categories | Specific Indications | Active Agent |
|---|---|---|
| Ophthalmic preparations | Legionnaires' disease | Erythromycin ethylsuccinate |
| | Neovascular (wet) age-related macular degeneration | Ranibizumab |
| | Subfoveal choroidal neovascularization due to age-related macular degeneration, pathologic myopia or presumed ocular histoplasmosis | Verteporfin |
| Antihistamine & Mast Cell Stabilizer Combinations | Prevention of itching associated with allergic conjunctivitis | Epinastine hydrochloride |
| | Ocular itching associated with allergic conjunctivitis | Olopatadine hydrochloride |
| Antihistamines & Combinations | Itchy eyes | Ketotifen |
| Anti-Infectives | Bacterial conjunctivitis | Azithromycin |
| | Bacterial conjunctivitis | Besifloxacin |
| | Corneal ulcer caused by bacteria | Levofloxacin |
| | Bacterial conjunctivitis | Levofloxacin |
| | Bacterial conjunctivitis | Moxifloxacin hydrochloride |
| Artificial Tears/Lubricants & Combinations | Increased tear production | Cyclosporine |
| Beta Adrenergic Blocking Agents & Combinations | Elevated intraocular pressure in patients with ocular hypertension or open-angle glaucoma | Timolol |
| | Reduction of elevated intraocular pressure in patients with glaucoma or ocular hypertension | Brimonidine tartrate and Timolol maleate |
| Carbonic Anhydrase Inhibitors & Combinations | Elevated intraocular pressure in patients with ocular hypertension or open-angle glaucoma | Dorzolamide hydrochloride |
| Mast Cell Stabilizers | Prevention of itching of the eye due to allergic conjunctivitis | Pemirolast potassium |
| Prostaglandins | Reduction of elevated intraocular pressure in patients with open angle glaucoma or ocular hypertension | Bimatoprost |
| | Reduction of elevated intraocular pressure in patients with open angle glaucoma or ocular hypertension | Travoprost |
| Sympathomimetics & Combinations | Reduction of elevated intraocular pressure in patients with open angle glaucoma or ocular hypertension | Brimonidine tartrate |

In addition to the active agents recited in Table A, other suitable active agents include, but are not limited to, antibodies, antibody fragments (e.g., mini-antibodies, Fab, and antigenic binding domain rabbit antibody IgG), adnectins, insulin, interleukins, colony stimulating factors, hormones (e.g., growth hormone, vasopressin, luteinizing hormone-releasing hormone), erythropoietin, interferons, aptamers (e.g., PEGylated aptamers), siRNA, antisense RNA, nucleotides (and/or modified nucleotides), PEGylated proteins, enzymes, blood clotting factors, cytokines, growth factors, vaccine agents (e.g., microorganisms or components thereof, toxoids), small molecule drugs, or combinations thereof. The active agent can be natural, synthetic, or a partially synthetic product. In one embodiment, the active agent is a recombinant protein. In another embodiment, the active agent is a synthetic oligonucleotide.

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA.

Accordingly, in one embodiment, the active agent can be a gene silencing agent, such as siRNA. The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

Other suitable active agents include rapamycin, dexamethasone, paclitaxel, triamcinolone, bevacizumab, trastuzumab, and rituximab, as well as other active agents described in the *Physician's Desk Reference*, 64$^{th}$ Edition (2010).

The formulations described herein can be used to treat a variety of conditions by using a suitable active agent in the injectable formulation. Such conditions or diseases include, but are not limited to, retinal diseases, front of the eye diseases, inflammatory diseases, autoimmune diseases, or a combination thereof. Certain specific conditions that can be treated using a formulation described herein include keratoconjunctivitis sicca (KCS) or dry eye syndrome, aphakia; pseudophakia; blepharospasm; cataract; conjunctival diseases; conjunctivitis; corneal diseases; corneal ulcer; eyelid diseases; lacrimal apparatus diseases; lacrimal duct obstruction; myopia; presbyopia; pupil disorders; refractive disorders and strabismus, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema (DME); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Treating combinations of any of the aforementioned conditions is also an intended embodiment of this disclosure. Some suitable diseases, disorders and/or conditions are also described in Table A above.

Injectable Pharmaceutical Formulations and Resulting Implants

When the composition is administered by injection, an implant will form in vivo, upon contact with bodily fluids. When the composition is administered as an implant, the implant can be pre-formed and subsequently introduced within the body of a patient. Either way, an effective amount of the active agent can be released by diffusion, erosion, absorption, degradation, or a combination thereof, as the solid implant biodegrades in the patient.

The nature and amount of solvent, polymer, crosslinking agent, and active agent can be selected such that the desired duration of administration is achieved. For example, the formulation can be administered to release an effective amount of active agent over a suitable period of time, for example, of about once a week to about once per 12 months, about once a week to about once per 6 months, about once a week to about once per 3 months, or about once a week to about once per month.

The nature and amount of solvent, polymer, crosslinking agent, and active agent can be selected such that the desired composition or formulation will have an acceptable chemical and/or physical stability. Such stability can be, for example, for about one month to about 6 months, to about 1 year, up to about 2 years.

By appropriate choice of solvent, water migration from the aqueous environment surrounding the implant is restricted, and an active agent is released to the subject over a period of time, thus providing for delivery of the active agent with a controlled burst of active agent, or little or no initial burst, which is followed by sustained release thereafter. The implant formed is bioerodible, such that the implant does not have to be surgically removed after the active agent is depleted from the implant.

Water uptake and burst can be controlled by using polymer-solvent ratios where the solvent is substantially immiscible in water, so as to control the rate of water migration into the polymer implant and ultimately control the burst of active agent and the sustained delivery of the active agent. Generally, the compositions will form an implant upon exposure to an aqueous environment, such as mammalian tissue. Furthermore, while the organogel implant will slowly harden when subjected to an aqueous environment, the hardened implant can maintain an elastic (non-rigid) quality as a result of a glass transition temperature of about 37° C., or less. In some embodiments, the formulation will have a viscosity of about 100 cP to about 1000 cP prior to injection and crosslinking.

Carriers

Carriers can be administered in combination with the active agent to improve delivery of the active agents to the targeted tissues and cells. Carriers can also protect the active agent from damage or premature degradation.

In various embodiments, a nucleic acid can be used as an active agent, and a carrier can be attached to the nucleic acid to form a nucleic acid complex. Carrier agents used with embodiments of the invention can include those compounds that can be complexed with nucleic acids in order to preserve the activity of the nucleic acids during manufacturing and delivery processes. Typically, nucleic acid/carrier complexes self-assemble when brought into contact with one another, for example, in an aqueous solution. For example, a complex may form due to the charge-charge interactions between a negatively charged nucleic acid and a positively charged carrier agent. In some instances, particles (e.g., micelles, lipoplexes or liposomes) can be formed when the active agent interacts with a carrier agent. Exemplary classes of suitable carrier agents can include cationic compounds and charge neutral compounds.

Carrier agents can include cationic polymers that are capable of efficiently condensing the active agent into nanoparticles, termed "polyplexes", by self-assembly via electrostatic interactions. Sometimes the cationic polymer includes one or more functional groups that can be modified with ligands, such as cell-targeting molecules. Examples of cationic polymers include, but are not limited to polycations containing cyclodextrin, histones, cationized human serum albumin, aminopolysaccharides such as chitosan, peptides such as poly-L-lysine, poly-L-ornithine, and poly(4-hydroxy-L-proline ester, and polyamines such as polyethylenimine (PEI), polypropylenimine, polyamidoamine dendrimers, and poly(beta-aminoesters).

Another class of carrier includes cationic lipids. Cationic lipid carriers are commercially available and include, but are not limited to 1,2-dioleoyl-3-trimethylammonium propane (DOTAP), N-methyl-4-(dioleyl)methylpyridinium (SAINT-2), 3β-[N—(N',N-dimethyl-aminoethane)-carbamoyl]cholesterol (DC-Chol), or a gemini surfactant (e.g., a surfactant having two conventional surfactant molecules chemically bonded together by a spacer), such as GS1 (a sugar-based gemini surfactant), as well as the neutral lipid dioleoylphosphatidyl-ethanolamine (DOPE) and cholesterol. Addition of polyanionic nucleic acids to mixtures of cationic lipids or liposomes results in the self-assembly of particles termed "lipoplexes." Other carrier agents can include solid nucleic acid lipid nanoparticles (SNALPs), liposomes and the like. In one embodiment, the carrier can be conjugated to one or more molecules that target specific cell types. Examples of targeting agents include antibodies and peptides that recognize and bind to specific cell surface molecules.

In some embodiments, carriers can include peptides that facilitate delivery of an active agent to a cell of interest. For example, exemplary peptides can associate with a nucleic acid and facilitate delivery of that nucleic acid to the cytoplasm of a cell. The term "peptide" includes any compound containing two or more amino-acid residues joined by amide bond(s) formed from the carboxyl group of one amino acid (residue) and the amino group of the next amino acid. As such, peptides can include oligopeptides, polypeptides, and proteins.

In some embodiments, carrier can include peptides that have at least two domains, such as a cellular penetration domain and a nucleic acid binding domain. The term "cellular penetration domain" refers to a region of a peptide molecule that functions to facilitate entry of the molecule into a cell, and "nucleic acid binding domain" refers to a region of a peptide molecule that functions to bind with nucleic acids.

Many different peptides for targeted delivery of the active agent (e.g., a nucleic acid) are contemplated herein. One exemplary peptide, known as MPG, is a 27 amino acid bipartite amphipathic peptide composed of a hydrophobic domain derived from HIV-1 gp41 protein and a basic domain from the nuclear localization sequence (NLS) of SV40 large T antigen (GALFLGFLGAAGSTMGAWSQPKKKRKV), commercially available as the N-TER Nanoparticle siRNA Transfection System (from Sigma-Aldrich, St. Louis, Mo.). Another exemplary peptide, known as MPGΔ$^{NLS}$, is also a 27 amino acid bipartite amphipathic peptide (GALFLGFLGAAGSTMGAWSQPKSKRKV). Other exemplary peptides can include poly-arginine fusion peptides. Yet other exemplary peptides include those with protein transduction domains linked with a double-stranded RNA binding domain, such as PTD-DRBD protein.

The present invention provides for the following Embodiments, which are intended to illustrate the above invention and should not be construed as to narrow its scope.

Embodiments

[1] The present invention provides for an injectable formulation comprising: an active agent;
a non-aqueous, aprotic, biocompatible solvent system, wherein the solvent system comprises one or more solvents, and at least one of the solvents is non-miscible with water;
a plurality of polymers that each include a plurality of hydroxyl groups; and
a plurality of crosslinking agents, wherein the crosslinking agent comprises X—($C_1$-$C_{16}$)alkyl-X or X—($CH_2CH_2$—O)$_n$—$CH_2CH_2$—X where "n" is 0 to about 20, and each X is independently a chlorosilane group, a trialkoxysilane group, or —NCO;
wherein the solvent system is chemically inert with respect to the crosslinking agents, and the formulation is substantially free of water.

[2] The present invention also provides for the formulation of embodiment [1], wherein the polymer having hydroxyl groups comprises one or more of: polysaccharides, PEG-PLA block copolymers having two or more free hydroxyl groups, polyglycerol, esterified polyglycerol having two or more free hydroxyl groups, polyvinylacetate (PVA) having two or more free hydroxyl groups, a star-shaped PLA, or a comb-shaped PLA.

[3] The present invention also provides for the formulation of embodiment [1] or [2], wherein the polymer having hydroxyl groups comprises a polysaccharide that have a degree of substitution by optionally substituted ($C_2$-$C_{12}$) alkanoate groups of about 0.25 to about 2.

[4] The present invention also provides for the formulation of any one of embodiments [1]-[3], wherein the active agent comprises about 0.1 wt. % to about 30 wt. % of the formulation, the solvent system comprises about 10 wt. % to about 90 wt. % of the formulation, the polymers having hydroxyl groups comprise about 5 wt. % to about 50 wt. % of the formulation, and the crosslinking agents comprise about 1 wt. % to about 50 wt. % of the formulation.

[5] The present invention also provides for the formulation of any one of embodiments [1]-[4], wherein the polymer having hydroxyl groups is soluble in the biocompatible solvent system and the active agent is substantially insoluble in the non-aqueous biocompatible solvent system.

[6] The present invention also provides for the formulation of any one of embodiments [1]-[5], wherein the molar ratio of reactive groups on the crosslinking agents to free hydroxyl groups of the polymers having hydroxyl groups is about 0.1 to about 5.

[7] The present invention also provides for the formulation of any one of embodiments [1]-[6], wherein the active agent comprises a peptide, a protein, a gene, a polynucleotide or an analog or complex thereof, a nucleotide, a nucleoside, or a small molecule drug.

[8] The present invention also provides for the formulation of any one of embodiments [1]-[7], wherein the polymer has a viscosity of at least about 100 cP in the biocompatible solvent system at 37° C.

[9] The present invention also provides for the formulation of any one of embodiments [1]-[8], wherein X comprises a chlorosilane group wherein the chlorosilane group is —Si(Me)$_2$Cl or —Si(Et)$_2$Cl; X comprises a trialkoxysilane group wherein the trialkoxysilane group is —Si(OMe)$_3$ or —Si(OEt)$_3$; or a combination thereof.

[10] The present invention also provides for an in vivo biodegradable crosslinked matrix comprising:
a non-aqueous aprotic biocompatible solvent system wherein the solvent system comprises one or more solvents and at least one of the solvents is non-miscible with water;
a plurality of polymers that each include a plurality of hydroxyl groups, where a plurality of the polymers are crosslinked by:
—(Y)$_2$Si—($C_1$-$C_{16}$)alkyl-Si(Y)$_2$— groups;
—(Y)$_2$Si—($CH_2CH_2$—O)$_n$—$CH_2CH_2$—Si(Y)$_2$— groups where n is 0 to about 20;
—C(=O)NH—($C_1$-$C_{16}$)alkyl-Si(Y)$_2$— groups;
—C(=O)NH—($CH_2CH_2$—O)$_n$—$CH_2CH_2$—Si(Y)$_2$— groups where n is 0 to about 20;
—C(=O)NH—($C_1$-$C_{16}$)alkyl-NH—C(=O)— groups;

—C(=O)NH—(CH$_2$CH$_2$—O)$_n$—CH$_2$CH$_2$—NH—C(=O)— groups where n is 0 to about 20; or a combination thereof; where each Y is independently —OH, —O-alkyl, or alkyl; and an active agent that is dissolved or dispersed throughout the crosslinked matrix.

[11] The present invention also provides for the formulation of embodiment [10], wherein degree of crosslinking of each polymer averages about 0.1 to about 2 per monomer of the polymer.

[12] The present invention also provides for the formulation of any embodiment [10] or [11], wherein the active agent is insoluble in the insoluble in the non-aqueous biocompatible solvent system and the active agent comprises homogeneously dispersed particles of about 1 μm to about 10 μm in diameter.

[13] The present invention also provides for the formulation of any one of embodiments [10]-[12], wherein less than about 20 wt. % of the active agent is released from the matrix within the first 20 days of deposit within a subject.

[14] The present invention also provides for the formulation of any one of embodiments [10]-[13], wherein the plurality of polymers comprise crosslinked substituted polysaccharides of Formula I:

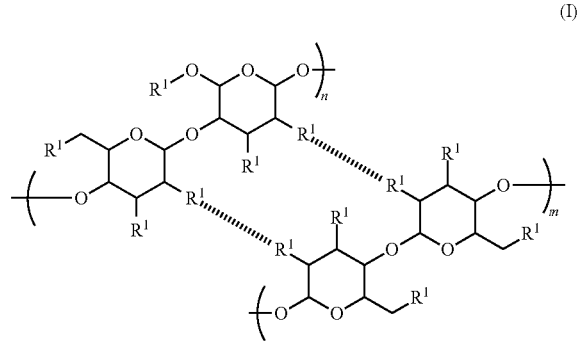

(I)

wherein each R$^1$ is independently OH, —OSi(alkyl)$_3$, or an optionally substituted (C$_2$-C$_{12}$)alkanoate, or any two R$^1$ groups together form a crosslinking moiety, wherein each crosslinking moiety independently comprises:

—OSi(Y)$_2$—(C$_1$-C$_{16}$)alkyl-Si(Y)$_2$O—;
—OSi(Y)$_2$—(CH$_2$CH$_2$—O)$_n$—CH$_2$CH$_2$—Si(Y)$_2$O— where n is 0 to about 20;
—O—C(=O)NH—(C$_1$-C$_{16}$)alkyl-Si(Y)$_2$O—;
—O—C(=O)NH—(CH$_2$CH$_2$—O)$_n$—CH$_2$CH$_2$—Si(Y)$_2$O— where n is 0 to about 20;
—O—C(=O)NH—(C$_1$-C$_{16}$)alkyl-NH—C(=O)O—; or
—O—C(=O)NH—(CH$_2$CH$_2$—O)$_n$—CH$_2$CH$_2$—NH—C(=O)O— where n is 0 to about 20; where each Y is independently —OH, —O-alkyl, or alkyl;

the dashed lines in Formula I represent two optional locations of crosslinking; and n and m are selected so that each base polysaccharide has a molecular weight of about 10 kDa to about 1000 kDa.

[15] The present invention also provides for the formulation of embodiment [14], wherein the crosslinked substituted polysaccharides of Formula I are crosslinked between one or more of: a primary R$^1$ group and primary R$^1$ group on a different polysaccharide, a primary R$^1$ group and a secondary R$^1$ group on a different polysaccharide, a secondary R$^1$ group and secondary R$^1$ group on a different polysaccharide, or a primary or secondary R$^1$ group and a hydroxyl substituent on R$^1$ when R$^1$ is a substituted a (C$_2$-C$_{12}$)alkanoate on a different polysaccharide.

[16] The present invention also provides for a method of delivering an active agent to a subject comprising:
injecting a formulation comprising:
an active agent;
a non-aqueous, aprotic, biocompatible solvent system, wherein the solvent system comprises one or more solvents and at least one of the solvents is non-miscible with water;
a plurality of polymers that each include a plurality of hydroxyl groups; and
a plurality of crosslinking agents, wherein the crosslinking agent comprises X—(C$_1$-C$_{16}$)alkyl-X or X—(CH$_2$CH$_2$—O)$_n$—CH$_2$CH$_2$—X where "n" is 0 to about 20, and each X is independently a chlorosilane group, a tri(C$_1$-C$_3$)alkoxysilane group, or —NCO;
wherein the solvent system is chemically inert with respect to the crosslinking agents and the formulation is substantially free of water; and
the formulation forms a gel matrix within the subject and the gel matrix becomes crosslinked when the polysaccharides and crosslinking agents are contacted by fluids in the body of the subject; and
the matrix releases the active agent, over a period of weeks, to the body of the subject; thereby delivering the active agent to the subject.

[17] The present invention also provides for the method of embodiment [16], wherein the injecting comprises injecting the formulation into tissue of the subject.

[18] The present invention also provides for the method of embodiment [16], wherein the injecting comprises injecting ex vivo, allowing the resulting matrix to crosslink by contact with ambient humidity to form an implant, followed by inserting the resulting implant into the patient.

[19] The present invention also provides for the method of any one of embodiments [16]-[18], wherein the active agent comprises about 0.1 wt. % to about 30 wt. % of the formulation, the solvent system comprises about 10 wt. % to about 90 wt. % of the formulation, the polymer comprise about 5 wt. % to about 50 wt. % of the formulation, and the crosslinking agents comprise about 1 wt. % to about 50 wt. % of the formulation.

[20] The present invention also provides for the method of any one of embodiments [16]-[17] and [19], wherein the formulation is injected into the vitrius humor of the eye of the subject, the formulation is injected to a site under the skin of the subject, or the formulation is injected intramuscularly to the subject.

[21] The present invention also provides for the method of any one of embodiments [16]-[20], wherein the active agent comprises a peptide, a protein, a gene, a polynucleotide or an analog or complex thereof, a nucleotide, a nucleoside, or a small molecule drug.

[22] The present invention also provides for the method of any one of embodiments [16]-[21], wherein the method comprises the active agent in an effective amount to treat keratoconjunctivitis sicca (KCS) or dry eye syndrome, aphakia; pseudophakia; blepharospasm; cataract; conjunctival diseases; conjunctivitis; corneal diseases; corneal ulcer; eyelid diseases; lacrimal apparatus diseases; lacrimal duct obstruction; myopia; presbyopia; pupil disorders; refractive disorders and strabismus, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema (DME); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, or glaucoma.

[23] The present invention also provides for the method of any one of embodiments [16]-[22], wherein less than about 15 wt. % of the initial mass of the active agent is delivered to the subject from the matrix within the first 10 post-injection days.

[24] The present invention also provides for the method of any one of embodiments [16]-[23], wherein the active agent is delivered to the subject from the matrix at a rate of not more than about 10 wt. % of the initial mass of the active agent per week, after the first week post-injection.

[25] The present invention also provides for the method of any one of embodiments [16]-[24], wherein the method delivers an effective amount of the active agent in a sustained release profile in an amount effective to treat a disease or condition recited in embodiment [22].

[26] The present invention also provides for a formulation of any one of embodiments [1]-[14], for the treatment of a disease.

[27] The present invention also provides for a formulation of any one of embodiments [1]-[14], for the treatment of at least one of the following diseases or disorders: keratoconjunctivitis sicca (KCS) or dry eye syndrome, aphakia; pseudophakia; blepharospasm; cataract; conjunctival diseases; conjunctivitis; corneal diseases; corneal ulcer; eyelid diseases; lacrimal apparatus diseases; lacrimal duct obstruction; myopia; presbyopia; pupil disorders; refractive disorders and strabismus, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema (DME); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Table 3 provides an identification of the specific polymers used in the examples below. The abbreviations "Glu2", "Glu6D", and "MO40" refer to maltodextrin polymers having an approximate molecular weight as shown in the table. The abbreviations "Hex" and "Pro" refer to hexanoate and propanoate pendant groups on the maltodextrin polymers. The number after "Hex" and "Pro" refers to the degree of substitution on the polymers.

TABLE 1

Examples of Hydrophobic Polymers that can be Crosslinked

| Designation | Maltodextrin $M_w$ | Pendent Hydrophobic Group |
|---|---|---|
| Glu2-Hex-x | 330 kDa | Hex = hexanoate |
| Glu2-Pro-x | 330 kDa | Pro = Propanoate |
| Glu6D-Hex-x | 150 kDa | Hex = hexanoate |
| MO40-Hex-x | 50 kDa | Hex = hexanoate |

X = degree of substitution (DS); final MW of polymer depends on DS.

Example 1

Crosslinked Organogel Formation

Crosslinked organogels were formed from a variety of polymers, such as the maltodextrin derivatives represented in Table 1. Crosslinking agents having bis-chlorosilane groups were used to as a proof of concept and to analyze the resulting crosslinked polymers. Formation of organogels using bis-trialkoxysilyl ether crosslinkers was then carried out in the presence of moisture (e.g., water) to replicate physiological conditions. Suitable hydrogels also formed by this procedure.

Scheme 1 illustrates the use of bis-silane crosslinkers to form a gel with hydrophobic polymers (see Table 1) in an organic solvent. Catalytic amounts of either an acid, such as acetic acid, or a base, such as triethylamine, were useful to facilitate crosslinking.

Scheme 1.

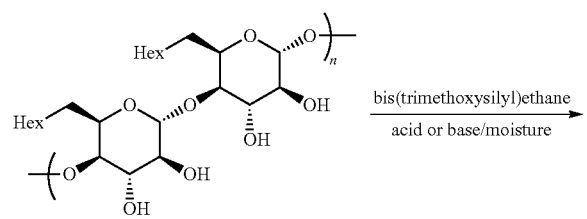

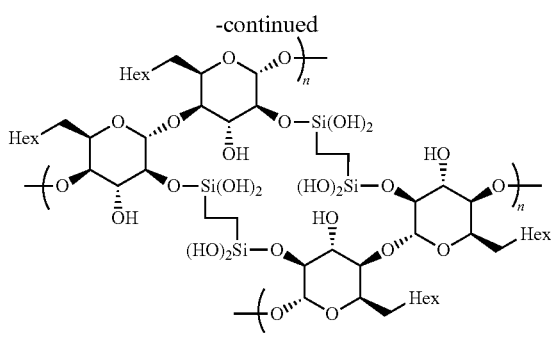

where "Hex" represents hexanoate "pendent" groups. Other pendant groups can be used, as indicated by Table 1, including any $(C_2-C_{12})$alkanoate group optionally substituted by one or more hydroxy or amino groups. Any suitable crosslinking group can be used, as described above in the description of crosslinking moieties.

Methods.

G2-Hex-1.6 was dissolved in either benzyl benzoate or ethyl heptanoate at a concentration of 300 mg/mL at approximately 60° C. In duplicate, freshly cooled solutions were aliquotted in 33 μL total (10 mg of polymer) at benzyl benzoate/ethyl heptanoate ratios of 100:0, 75:25, 50:50, 25:75 and 0:100. Spray-dried Fab particles (2.9 mg; 70% protein, 30% trehalose) were mixed into the solutions. The spray-dried Fab particles can be replaced by any suitable active agent, as described in the specification above.

To one series, 5 μL of triethylamine and 5 μL of bis(dimethylchlorosilyl)octane was added. Gels formed immediately using this highly reactive crosslinker. To the second series, 2 μL of glacial acetic acid and 5 μL of bis(trimethoxysilyl) ethane was added. The samples were left uncapped to react at room temperature, for approximately 1-3 days. The gels were then used for controlled release experiments.

Results.

In each experiment, a gel was obtained. The chlorosilane crosslinked gels formed rapidly and became white organogels. The trimethoxysilane crosslinked organogels formed gels more slowly, and remained clear at first, similar to gels formed in ethyl heptanoate. During the release of proteins in the controlled release experiments, each of the gels became white or more opaque over time.

Figure 1:
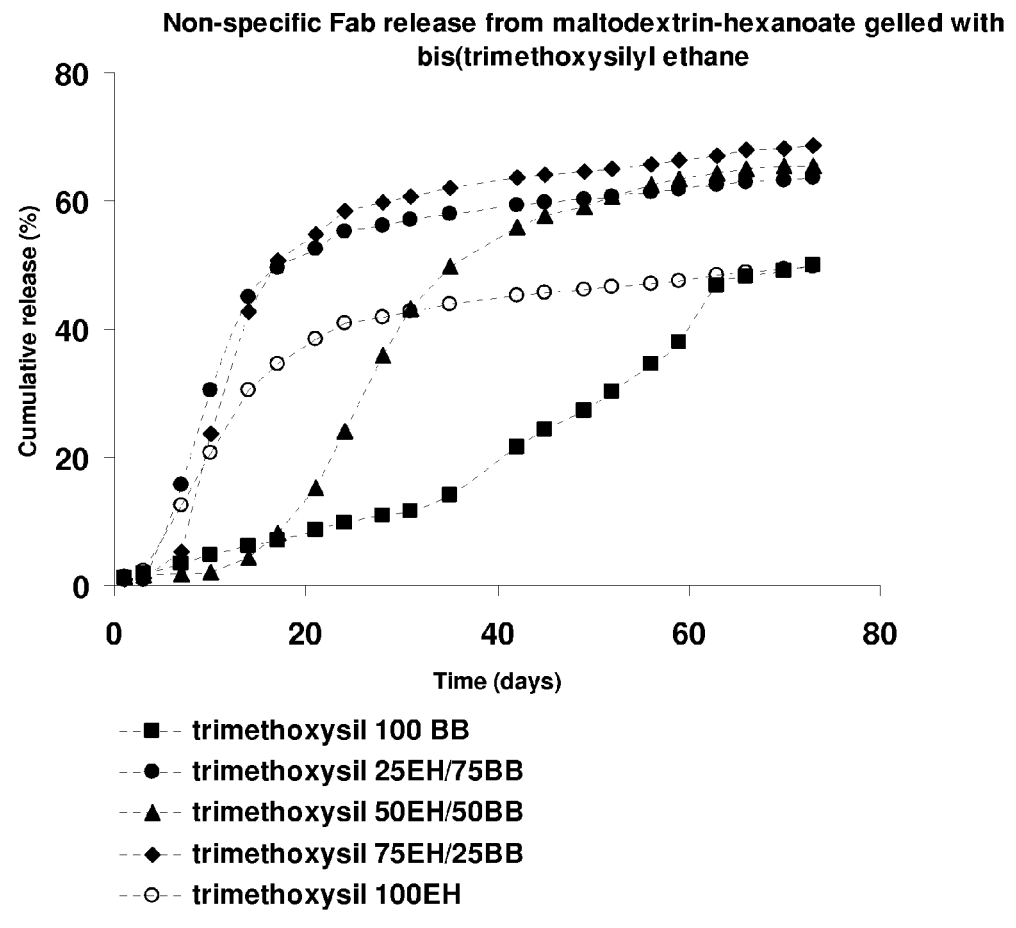

FIG. 1 illustrates controlled release experiments where the release of 20 wt. % Fab from various organogels formed from chlorosilane derived crosslinking moieties was monitored for more than 70 days.

FIG. 2 illustrates controlled release experiments where the release of 20 wt. % Fab from various organogels formed from trimethoxysilane-containing crosslinking moieties was monitored for more than 70 days.

These results show that the crosslinked organogels provide compositions for the sustained release of an active agent over the course of days, weeks, or months, with little or no burst effect.

Example 2

Bifunctional Crosslinkers

Hydrophobic polymer "Glu2-Hex-1.6" (200 mg) was dissolved in 660 μL of benzylbenzoate to provide a 300 mg/mL solution. Triethylamine (20 μL) was added to the solution and the mixture was then vortexed. Thirty-three μL of the solution was pipetted (assumed 10 mg of polymer) into 9 microcentrifuge tubes.

The molecular weight (m.w.) per sugar unit of the maltodextrin polymer that is grafted with hexanoate at DS1.6 was 162.14 Da. Hexanoate groups have a m.w. of 100.16 Da, therefore, 1.6×100.16+162.14=322.4 mol/g (average m.w. of a DS1.6 substituted maltodextrin monomer). Thus one gram of Glu2-Hex-1.6=3.1 mmol of the substituted units. A total three hydroxyl groups per sugar unit are available for substitution, therefore there are 1.4 hydroxyl groups left on average in Glu2-Hex-1.6. Therefore, 4.3 mmol of free hydroxyl groups per gram polymer are available for crosslinking, or 43 μmol free hydroxyl groups per 10 mg.

To the vials, 5, 10 or 20 μL of the following crosslinkers was added:

A. To vials 1, 2, and 3: 1,8-bis(dimethylchlorosilyl)octane was added:

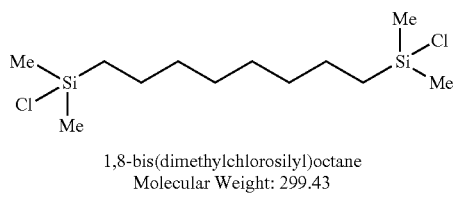 [SMILES: C[Si](C)(Cl)CCCCCCCC[Si](C)(C)Cl]

1,8-bis(dimethylchlorosilyl)octane
Molecular Weight: 299.43 d=0.946 g/mL.
5 μL→16.6 μmol→33 μmol crosslinking groups=a 1:0.77 ratio of free —OH groups to crosslinking groups;
10 μL→0.033 μmol→66 μmol crosslinking groups=a 1:1.5 ratio;
20 μL→0.066 μmol→133 μmol crosslinking groups=a 1:3.1 ratio.

B. To vials 4, 5, and 6: 1,2-bis(trimethoxysilyl)ethane was added:

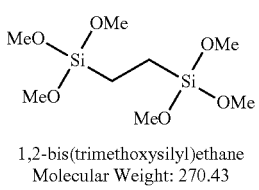

1,2-bis(trimethoxysilyl)ethane
Molecular Weight: 270.43 d=0.957 g/mL.
5 μL→18.0 μmol→36 μmol crosslinking groups=a 1:0.84 ratio;
10 μL→0.036 μmol→72 μmol crosslinking groups=a 1:1.67 ratio;
20 μL→0.072 μmol→144 μmol crosslinking groups=a 1:3.3 ratio.

C. To vials 7, 8, and 9: triethoxy(3-isocyanatopropyl)silane was added:

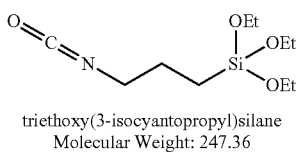 [SMILES: CCO[Si](CCCN=C=O)(OCC)OCC]

triethoxy(3-isocyantopropyl)silane
Molecular Weight: 247.36 d=0.95 g/mL.
5 μL→19.2 μmol→38 μmol crosslinking groups=a 1:0.88 ratio;

10 μL→0.038 μmol→77 μmol crosslinking groups=a 1:1.76 ratio;
20 μL→0.077 μmol→154 μmol crosslinking groups=a 1:3.5 ratio.

To vials 1, 2 and 3, an additional 10 μL of TEA was added, which resulted in fast gelling in vial 1 and formation of white precipitate. Vials 2 and 3 gelled as well, but slower with less formation of precipitate.

Vials 4 and 7 gelled when left at room temperature (~23° C.) for approximately 2.5 days, becoming hard gels. Vial 4 was formed a rigid gel, and vial 7 formed a brittle gel. Each of the other vials gelled to less rigid gels.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An injectable formulation comprising:
an active agent;
a non-aqueous, aprotic, biocompatible solvent system, wherein the solvent system comprises one or more solvents, and at least one of the solvents is non-miscible with water;
a plurality of polymers that each include a plurality of free hydroxyl groups; and
a plurality of crosslinking agents, wherein the crosslinking agent comprises X—$(C_1$-$C_{16})$alkyl-X or X—$(CH_2CH_2$—$O)_n$—$CH_2CH_2$—X where n is 0 to about 20, and each X is independently a chlorosilane group, a trialkoxysilane group, or —NCO, the crosslinking agents in solution with but not bonded to the plurality of polymers;
wherein the solvent system is chemically inert with respect to the crosslinking agents, and the formulation is substantially free of water.

2. The formulation of claim 1, wherein the polymer having hydroxyl groups comprises one or more of: polysaccharides, PEG-PLA block copolymers having two or more free hydroxyl groups, polyglycerol, esterified polyglycerol having two or more free hydroxyl groups, polyvinylacetate (PVA) having two or more free hydroxyl groups, a star-shaped PLA, or a comb-shaped PLA.

3. The formulation of claim 1, wherein the polymer having hydroxyl groups comprises a polysaccharide that have a degree of substitution by optionally substituted $(C_2$-$C_{12})$alkanoate groups of about 0.25 to about 2.

4. The formulation of claim 1, wherein the active agent comprises about 0.1 wt. % to about 30 wt. % of the formulation, the solvent system comprises about 10 wt. % to about 90 wt. % of the formulation, the polymers having hydroxyl groups comprise about 5 wt. % to about 50 wt. % of the formulation, and the crosslinking agents comprise about 1 wt. % to about 50 wt. % of the formulation.

5. The formulation of claim 1, wherein the polymer having hydroxyl groups is soluble in the biocompatible solvent system and the active agent is substantially insoluble in the non-aqueous biocompatible solvent system.

6. The formulation of claim 1, wherein the molar ratio of reactive groups on the crosslinking agents to free hydroxyl groups of the polymers having hydroxyl groups is about 0.1 to about 5.

7. The formulation of claim 1, wherein the active agent comprises a peptide, a protein, a gene, a polynucleotide or an analog or complex thereof, a nucleotide, a nucleoside, or a small molecule drug.

8. The formulation of claim 1, wherein the polymer has a viscosity of at least about 100 cP in the biocompatible solvent system at 37° C.

9. The formulation of claim 1, wherein X comprises a chlorosilane group wherein the chlorosilane group is —Si$(Me)_2$Cl or —Si$(Et)_2$Cl; X comprises a trialkoxysilane group wherein the trialkoxysilane group is —Si$(OMe)_3$ or —Si$(OEt)_3$; or a combination thereof.

10. A method of delivering an active agent to a subject comprising:
injecting a formulation comprising:
an active agent;
a non-aqueous, aprotic, biocompatible solvent system, wherein the solvent system comprises one or more solvents and at least one of the solvents is non-miscible with water;
a plurality of polymers that each include a plurality of free hydroxyl groups; and
a plurality of crosslinking agents, wherein the crosslinking agent comprises X—$(C_1$-$C_{16})$alkyl-X or X—$(CH_2CH_2$—$O)_n$—$CH_2CH_2$—X where n is 0 to about 20, and each X is independently a chlorosilane group, a tri$(C_1$-$C_3)$alkoxysilane group, or —NCO, the crosslinking agents in solution with but not bonded to the plurality of polymers;
wherein the solvent system is chemically inert with respect to the crosslinking agents and the formulation is substantially free of water; and
the formulation forms a gel matrix within the subject and the gel matrix becomes crosslinked when the polysaccharides and crosslinking agents are contacted by fluids in the body of the subject; and
the matrix releases the active agent, over a period of weeks, to the body of the subject; thereby delivering the active agent to the subject.

11. The method of claim 10, wherein the injecting comprises injecting the formulation into tissue of the subject.

12. The method of claim 10, wherein the injecting comprises injecting ex vivo, allowing the resulting matrix to crosslink by contact with ambient humidity to form an implant, followed by inserting the resulting implant into the patient.

13. The method of claim 10, wherein the active agent comprises about 0.1 wt. % to about 30 wt. % of the formulation, the solvent system comprises about 10 wt. % to about 90 wt. % of the formulation, the polymer comprise about 5 wt. % to about 50 wt. % of the formulation, and the crosslinking agents comprise about 1 wt. % to about 50 wt. % of the formulation.

14. The method of claim 10, wherein the formulation is injected into the vitrius humor of the eye of the subject, the formulation is injected to a site under the skin of the subject, or the formulation is injected intramuscularly to the subject.

15. The method of claim 10, wherein the active agent comprises a peptide, a protein, a gene, a polynucleotide or an analog or complex thereof, a nucleotide, a nucleoside, or a small molecule drug.

16. The method of claim 10, wherein the method comprises the active agent in an effective amount to treat keratoconjunctivitis sicca (KCS) or dry eye syndrome, aphakia; pseudophakia; blepharospasm; cataract; conjunctival diseases; conjunctivitis; corneal diseases; corneal ulcer; eyelid diseases; lacrimal apparatus diseases; lacrimal duct obstruction; myopia; presbyopia; pupil disorders; refractive disorders and strabismus, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema (DME); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, or glaucoma.

17. The method of claim 10, wherein less than about 15 wt. % of the initial mass of the active agent is delivered to the subject from the matrix within the first 10 post-injection days.

18. The method of claim 10, wherein the active agent is delivered to the subject from the matrix at a rate of not more than about 10 wt. % of the initial mass of the active agent per week, after the first week post-injection.

19. The method of claim 10, wherein the method delivers an effective amount of the active agent in a sustained release profile in an amount effective to treat a disease or condition recited in claim 16.

* * * * *